(12) United States Patent
Mathis

(10) Patent No.: US 7,775,968 B2
(45) Date of Patent: Aug. 17, 2010

(54) GUIDED ACCESS TO LUNG TISSUES

(75) Inventor: Mark Mathis, Fremont, CA (US)

(73) Assignee: PneumRx, Inc., Mountain View, CA (US)

( * ) Notice: Subject to any disclaimer, the term of this patent is extended or adjusted under 35 U.S.C. 154(b) by 696 days.

(21) Appl. No.: 11/153,295

(22) Filed: Jun. 14, 2005

(65) Prior Publication Data

US 2005/0288549 A1    Dec. 29, 2005

Related U.S. Application Data

(60) Provisional application No. 60/579,905, filed on Jun. 14, 2004.

(51) Int. Cl.
*A61B 1/00* (2006.01)
(52) U.S. Cl. .................. 600/104; 600/101; 600/114; 600/127; 600/153
(58) Field of Classification Search ............ 600/116, 600/153; 604/509
See application file for complete search history.

(56) References Cited

U.S. PATENT DOCUMENTS

| | | |
|---|---|---|
| 3,559,652 A | 2/1971 | Banitt et al. |
| 4,013,080 A | 3/1977 | Froning |
| 4,153,058 A | 5/1979 | Nehme |
| 4,233,984 A | 11/1980 | Walling |
| 4,245,624 A * | 1/1981 | Komiya ............ 600/106 |
| 4,479,792 A | 10/1984 | Lazarus et al. |
| 4,532,935 A | 8/1985 | Wang |
| 4,702,260 A | 10/1987 | Wang |
| 4,739,760 A | 4/1988 | Chin et al. |
| 4,766,906 A * | 8/1988 | Wang ............ 600/566 |
| 4,769,017 A | 9/1988 | Fath et al. |
| 4,880,015 A | 11/1989 | Nierman |
| 5,056,529 A | 10/1991 | de Groot |
| 5,084,012 A | 1/1992 | Kelman |
| 5,108,368 A | 4/1992 | Hammerslag et al. |
| 5,165,420 A | 11/1992 | Strickland |
| 5,186,167 A | 2/1993 | Kolobow |
| 5,190,546 A | 3/1993 | Jervis |
| 5,219,895 A | 6/1993 | Kelman |

(Continued)

FOREIGN PATENT DOCUMENTS

FR    2840796    12/2003

(Continued)

OTHER PUBLICATIONS

Hermanson, Greg T. 1996. *Bioconjugate Techniques*, San Diego: Academic Press, Inc.

(Continued)

*Primary Examiner*—Matthew J Kasztejna
(74) *Attorney, Agent, or Firm*—Townsend and Townsend and Crew LLP

(57) ABSTRACT

This invention relates generally to lung access devices and methods of using the devices to gain access to the interior of a lung or to the mediastinal space around the lung. In particular, the invention relates to auxiliary access devices and tools for use with conventional bronchoscopes or other endoscopes to enable the delivery of more and larger devices to a target site than is currently possible through a typical endoscope or bronchoscope.

24 Claims, 25 Drawing Sheets

U.S. PATENT DOCUMENTS

| | | | |
|---|---|---|---|
| 5,240,011 A | 8/1993 | Assa | |
| 5,261,889 A | 11/1993 | Laine et al. | |
| 5,312,329 A | 5/1994 | Beaty et al. | |
| 5,312,331 A | 5/1994 | Knoepfler | |
| 5,315,992 A | 5/1994 | Dalton | |
| 5,334,183 A | 8/1994 | Wuchinich | |
| 5,354,287 A | 10/1994 | Wacks | |
| 5,423,830 A * | 6/1995 | Schneebaum et al. | 606/115 |
| 5,484,401 A | 1/1996 | Rodriguez et al. | |
| 5,514,536 A | 5/1996 | Taylor | |
| 5,522,819 A * | 6/1996 | Graves et al. | 606/113 |
| 5,526,821 A | 6/1996 | Jamshidi | |
| 5,549,904 A | 8/1996 | Juergensen et al. | |
| 5,599,294 A | 2/1997 | Edwards et al. | |
| 5,660,175 A | 8/1997 | Dayal | |
| 5,660,185 A | 8/1997 | Shmulewitz et al. | |
| 5,697,365 A | 12/1997 | Pell | |
| 5,735,264 A | 4/1998 | Siczek et al. | |
| 5,736,132 A | 4/1998 | Juergensen et al. | |
| 5,750,657 A | 5/1998 | Edwardson et al. | |
| 5,762,070 A * | 6/1998 | Nagamatsu | 600/564 |
| 5,846,235 A | 12/1998 | Pasricha et al. | |
| 5,895,417 A * | 4/1999 | Pomeranz et al. | 607/101 |
| 5,916,210 A | 6/1999 | Winston | |
| 5,916,212 A | 6/1999 | Baust et al. | |
| 5,938,635 A | 8/1999 | Kuhle | |
| 5,954,636 A | 9/1999 | Schwartz et al. | |
| 5,957,919 A | 9/1999 | Laufer | |
| 5,964,770 A | 10/1999 | Flomenblit et al. | |
| 5,972,026 A | 10/1999 | Laufer et al. | |
| 5,978,697 A | 11/1999 | Maytal et al. | |
| 6,066,090 A * | 5/2000 | Yoon | 600/113 |
| 6,080,113 A | 6/2000 | Heneveld et al. | |
| 6,083,255 A | 7/2000 | Laufer et al. | |
| 6,123,665 A * | 9/2000 | Kawano | 600/104 |
| 6,174,323 B1 | 1/2001 | Biggs et al. | |
| 6,183,498 B1 | 2/2001 | DeVore et al. | |
| 6,196,966 B1 * | 3/2001 | Kerin et al. | 600/114 |
| 6,200,333 B1 | 3/2001 | Laufer | |
| 6,258,100 B1 | 7/2001 | Alferness et al. | |
| 6,267,732 B1 | 7/2001 | Heneveld et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,287,304 B1 | 9/2001 | Eggers et al. | |
| 6,293,951 B1 | 9/2001 | Alferness et al. | |
| 6,299,633 B1 | 10/2001 | Laufer | |
| 6,310,166 B1 | 10/2001 | Hickey et al. | |
| 6,312,428 B1 | 11/2001 | Eggers et al. | |
| 6,315,737 B1 | 11/2001 | Skinner | |
| 6,328,689 B1 | 12/2001 | Gonzalez et al. | |
| 6,328,701 B1 | 12/2001 | Terwilliger | |
| 6,352,503 B1 * | 3/2002 | Matsui et al. | 600/104 |
| 6,379,373 B1 | 4/2002 | Sawhney et al. | |
| 6,387,044 B1 | 5/2002 | Tachibana et al. | |
| 6,390,967 B1 | 5/2002 | Forman et al. | |
| 6,398,775 B1 | 6/2002 | Perkins et al. | |
| 6,402,701 B1 | 6/2002 | Kaplan et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,443,944 B1 * | 9/2002 | Doshi et al. | 606/1 |
| 6,447,534 B2 | 9/2002 | Cragg et al. | |
| 6,464,648 B1 | 10/2002 | Nakamura | |
| 6,474,340 B1 * | 11/2002 | Vaska et al. | 128/898 |
| 6,478,730 B1 | 11/2002 | Bala et al. | |
| 6,485,407 B2 | 11/2002 | Alferness et al. | |
| 6,485,436 B1 | 11/2002 | Truckai et al. | |
| 6,488,673 B1 | 12/2002 | Laufer et al. | |
| 6,491,706 B1 | 12/2002 | Alferness et al. | |
| 6,494,844 B1 | 12/2002 | Van Bladel et al. | |
| 6,494,897 B2 | 12/2002 | Sterman et al. | |
| 6,509,031 B1 | 1/2003 | Miller et al. | |
| 6,514,290 B1 | 2/2003 | Loomas | |
| 6,514,522 B2 | 2/2003 | Domb | |
| 6,527,761 B1 | 3/2003 | Soltesz et al. | |
| 6,537,195 B2 | 3/2003 | Forman | |
| 6,537,314 B2 | 3/2003 | Langberg et al. | |
| 6,540,694 B1 | 4/2003 | Van Bladel et al. | |
| 6,540,716 B1 | 4/2003 | Holm | |
| 6,549,800 B1 | 4/2003 | Atalar et al. | |
| 6,551,255 B2 | 4/2003 | Van Bladel et al. | |
| 6,551,302 B1 | 4/2003 | Rosinko et al. | |
| 6,552,172 B2 | 4/2003 | Marx et al. | |
| 6,558,337 B2 | 5/2003 | Dvorak et al. | |
| 6,568,387 B2 | 5/2003 | Davenport et al. | |
| 6,569,166 B2 | 5/2003 | Gonzalez | |
| 6,577,893 B1 | 6/2003 | Besson et al. | |
| 6,585,639 B1 | 7/2003 | Kotmel et al. | |
| 6,589,161 B2 | 7/2003 | Corcoran | |
| 6,592,559 B1 | 7/2003 | Pakter et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,622,731 B2 | 9/2003 | Daniel et al. | |
| 6,629,951 B2 | 10/2003 | Laufer et al. | |
| 6,632,222 B1 | 10/2003 | Edwards et al. | |
| 6,632,239 B2 | 10/2003 | Snyder et al. | |
| 6,632,243 B1 | 10/2003 | Zadno-Azizi et al. | |
| 6,634,363 B1 | 10/2003 | Danek et al. | |
| 6,638,275 B1 | 10/2003 | McGaffigan et al. | |
| 6,652,516 B1 | 11/2003 | Gough | |
| 6,652,520 B2 | 11/2003 | Moorman et al. | |
| 6,653,525 B2 | 11/2003 | Ingenito et al. | |
| 6,663,624 B2 | 12/2003 | Edwards et al. | |
| 6,679,264 B1 | 1/2004 | Deem et al. | |
| 6,682,520 B2 | 1/2004 | Ingenito | |
| 6,685,626 B2 | 2/2004 | Wironen | |
| 6,689,072 B2 | 2/2004 | Kaplan et al. | |
| 6,690,976 B2 | 2/2004 | Fenn et al. | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,709,408 B2 | 3/2004 | Fisher | |
| 6,709,456 B2 | 3/2004 | Langberg et al. | |
| 6,712,812 B2 | 3/2004 | Roschak et al. | |
| 6,716,180 B2 | 4/2004 | Fontenot | |
| 6,723,095 B2 | 4/2004 | Hammerslag | |
| 6,730,044 B2 | 5/2004 | Stephens et al. | |
| 6,736,822 B2 | 5/2004 | McClellan et al. | |
| 6,749,606 B2 | 6/2004 | Keast et al. | |
| 6,752,767 B2 | 6/2004 | Turovskiy et al. | |
| 6,752,812 B1 | 6/2004 | Truwit | |
| 6,758,824 B1 | 7/2004 | Miller et al. | |
| 6,768,425 B2 | 7/2004 | Flaherty et al. | |
| 6,770,066 B1 * | 8/2004 | Weaver et al. | 604/509 |
| 6,770,070 B1 | 8/2004 | Balbierz | |
| 6,789,545 B2 | 9/2004 | Littrup et al. | |
| 6,790,172 B2 | 9/2004 | Alferness et al. | |
| 6,790,185 B1 | 9/2004 | Fisher et al. | |
| 6,797,001 B2 | 9/2004 | Mathis et al. | |
| 6,807,446 B2 | 10/2004 | Fenn et al. | |
| 6,808,525 B2 | 10/2004 | Latterell et al. | |
| 6,817,973 B2 | 11/2004 | Merril et al. | |
| 6,825,091 B2 | 11/2004 | Bae et al. | |
| 6,827,086 B2 | 12/2004 | Shuman | |
| 6,827,683 B2 * | 12/2004 | Otawara | 600/123 |
| 6,830,756 B2 | 12/2004 | Hnojewyj | |
| 6,840,243 B2 | 1/2005 | Deem et al. | |
| 6,840,948 B2 | 1/2005 | Albrecht et al. | |
| 6,840,952 B2 | 1/2005 | Saker et al. | |
| 6,843,767 B2 | 1/2005 | Corcoran et al. | |

| | | |
|---|---|---|
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 * | 4/2005 | Herrmann .................. 600/104 |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,908,440 B2 | 6/2005 | Fisher |
| 6,918,881 B2 | 7/2005 | Miller et al. |
| 6,936,014 B2 | 8/2005 | Vetter et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 6,986,737 B2 * | 1/2006 | Suzuki et al. ............... 600/106 |
| 7,063,682 B1 * | 6/2006 | Whayne et al. .......... 604/95.04 |
| 7,175,619 B2 * | 2/2007 | Koblish et al. ................ 606/41 |
| 7,351,202 B2 * | 4/2008 | Long .......................... 600/106 |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | DeVore et al. |
| 2002/0128647 A1 | 9/2002 | Roschak et al. |
| 2002/0138074 A1 | 9/2002 | Keast et al. |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky |
| 2003/0029452 A1 | 2/2003 | Suki et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0069488 A1 | 4/2003 | Alferness et al. |
| 2003/0070676 A1 | 4/2003 | Cooper et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0038868 A1 | 2/2004 | Ingenito |
| 2004/0040555 A1 | 3/2004 | Tanaka |
| 2004/0049187 A1 | 3/2004 | Burnett et al. |
| 2004/0052850 A1 | 3/2004 | Schankereli |
| 2004/0055606 A1 | 3/2004 | Hendricksen et al. |
| 2004/0059263 A1 | 3/2004 | DeVore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078054 A1 | 4/2004 | Biggs et al. |
| 2004/0081676 A1 | 4/2004 | Schankereli et al. |
| 2004/0120849 A1 | 6/2004 | Stewart et al. |
| 2004/0133168 A1 | 7/2004 | Salcudean et al. |
| 2004/0158228 A1 | 8/2004 | Perkins |
| 2004/0172058 A1 | 9/2004 | Edwards et al. |
| 2004/0176801 A1 | 9/2004 | Edwards et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2005/0004599 A1 | 1/2005 | McNally-Heintzelman et al. |
| 2005/0015106 A1 | 1/2005 | Perkins et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0060041 A1 | 3/2005 | Phan et al. |
| 2005/0060042 A1 | 3/2005 | Phan et al. |
| 2005/0061322 A1 | 3/2005 | Freitag |
| 2005/0085801 A1 | 4/2005 | Cooper et al. |
| 2005/0096529 A1 | 5/2005 | Cooper et al. |
| 2005/0101836 A1 * | 5/2005 | Onuki et al. ................ 600/104 |
| 2005/0107783 A1 | 5/2005 | Tom et al. |
| 2005/0119614 A1 | 6/2005 | Mesky |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0009801 A1 | 1/2006 | McGurk et al. |
| 2006/0025815 A1 | 2/2006 | McGurk et al. |
| 2006/0167416 A1 | 7/2006 | Mathis et al. |
| 2007/0221230 A1 | 9/2007 | Thompson et al. |

FOREIGN PATENT DOCUMENTS

| | | |
|---|---|---|
| GB | 2324729 B | 1/2002 |
| WO | WO 00/13592 A1 | 3/2000 |
| WO | WO 01/13839 A1 | 3/2001 |
| WO | WO 02/00270 A1 | 1/2002 |
| WO | WO 02/00275 A1 | 1/2002 |
| WO | WO 02/02158 A1 | 1/2002 |
| WO | WO 03/077768 A1 | 9/2003 |
| WO | WO 2004/062505 A1 | 7/2004 |

WO WO 2004/086977 A1 10/2004

OTHER PUBLICATIONS

Lam, K.N. Sin Fai et al. 1998. X-Ray Diagnosis: A Physician's Approach. Singapore: Springer.

Rowe, Raymond C., et al. 2003. *Handbook of Pharmaceutical Excipients* 4th Edition. London: Pharmaceutical Press.

Slone, Richard M. et al. 2000. Body CT: A Practical Approach. New York: McGraw-Hill.

Stout, George H. et al. 1989. X-Ray Structure Determination: A Practical Guide, 2nd Edition. New York: John Wiley & Sons.

The United States Pharmacopeia, 29th Revision. 2006. The United States Pharmacopeial Convention.

Mathis, M., U.S. Appl. No. 11/286,445 entitled "Steerable Device for Accessing a Target Site and Methods", filed Nov. 23, 2005.

McGurk, E. et al., U.S. Appl. No. 11/178,243 entitled "Lung Device With Sealing Features", filed Jul. 8, 2005.

\* cited by examiner

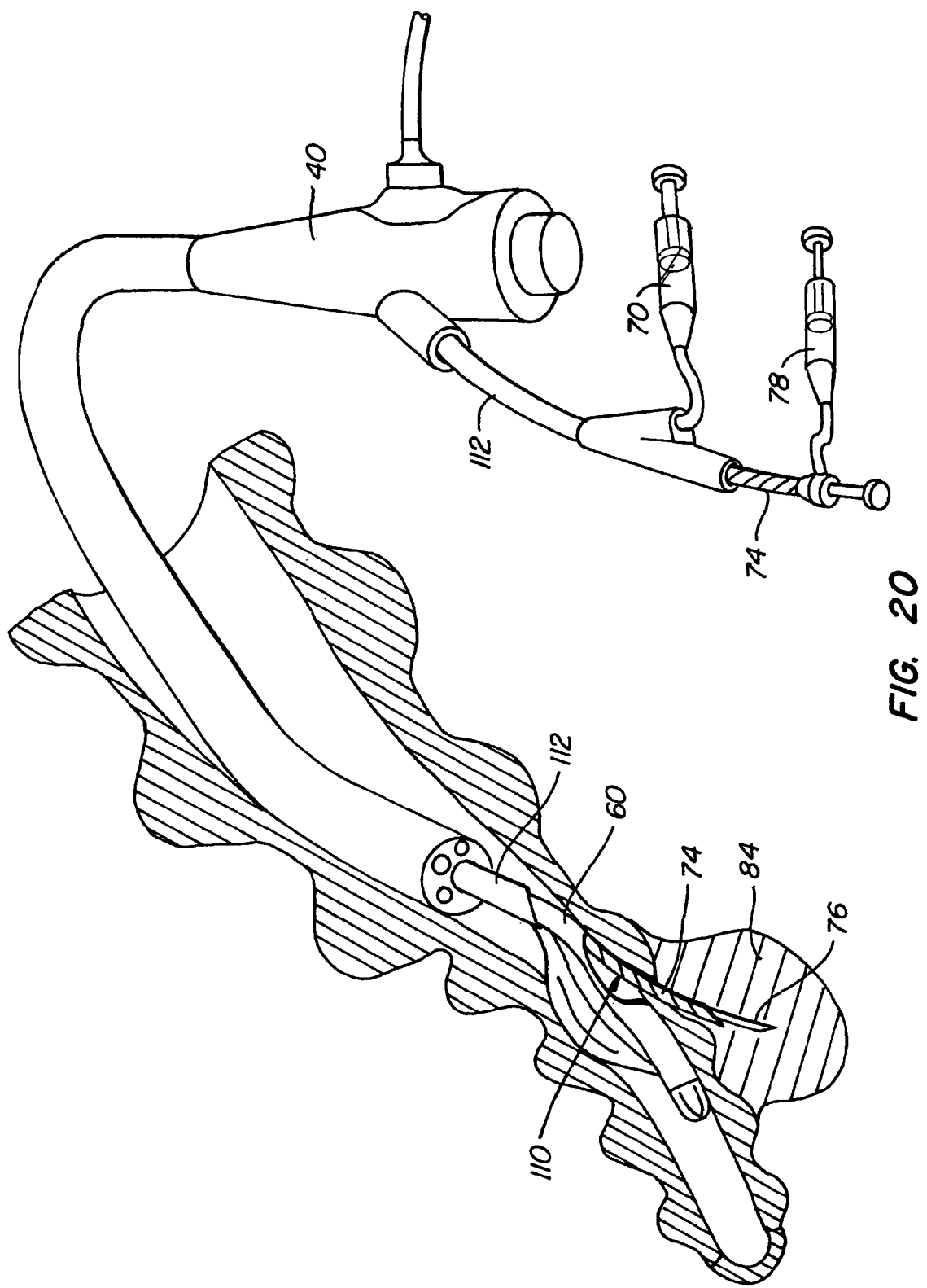

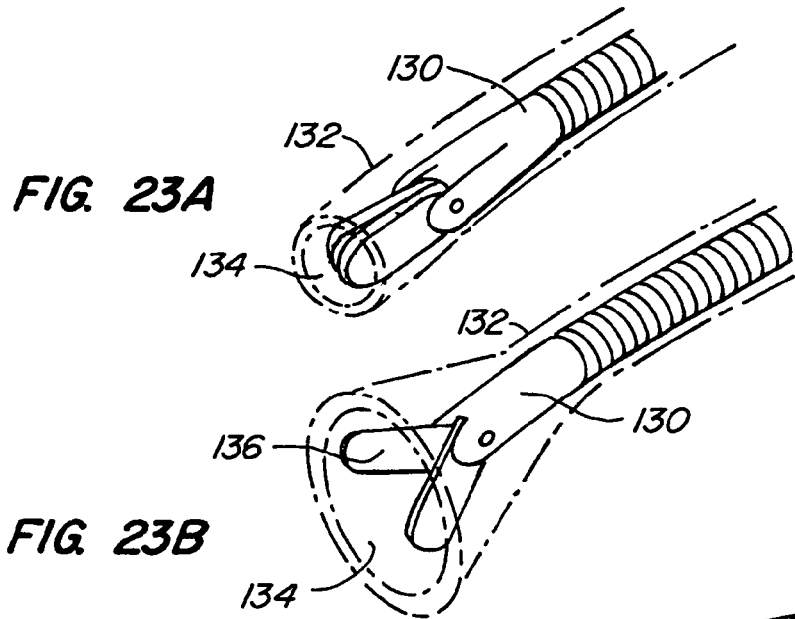
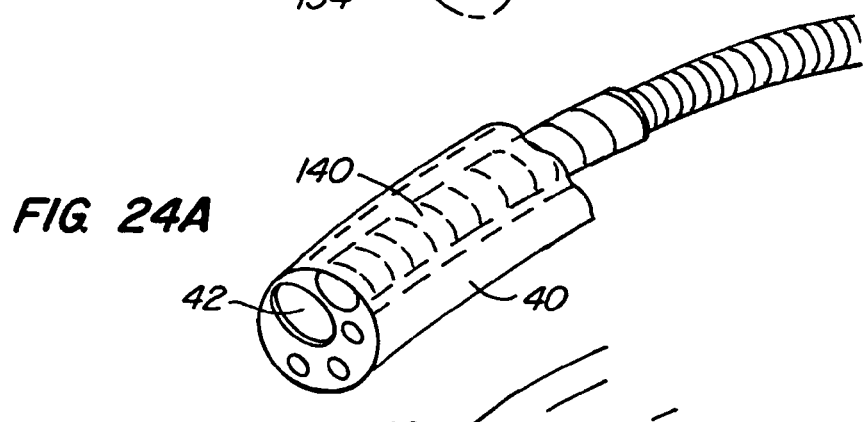
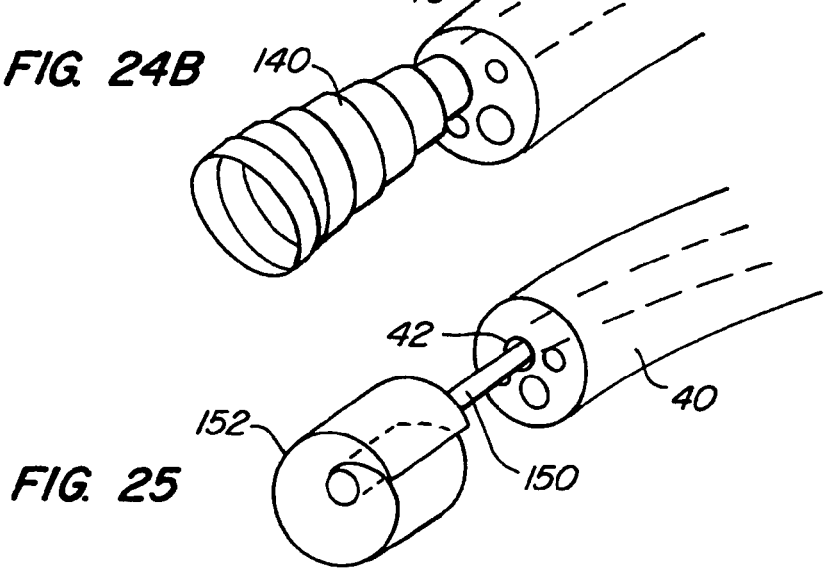

GUIDED ACCESS TO LUNG TISSUES

CROSS-REFERENCE TO RELATED APPLICATIONS

This application claims the priority benefit of U.S. Provisional Application Ser. No. 60/579,905 filed Jun. 14, 2004, which is hereby incorporated herein by reference in its entirety.

BACKGROUND OF THE INVENTION

This invention relates generally to the use of bronchoscopes and other devices to gain access to the interior of a lung or to the mediastinal space around the lung. In particular, the invention relates to auxiliary access devices and tools for use with conventional bronchoscopes or other endoscopes to enable the delivery of more and larger devices to a target site than is currently possible through a typical endoscope or bronchoscope.

Most bronchoscopy cases use the bronchoscope simply as a tool to access the bronchi (transnasal, oral or trachea access to the lung) and possibly visualize abnormal colors from adjacent pathologic tissue. Most bronchoscope-based biopsies target tissues that lie outside the bronchi trunk; thus, the interventionalist needs external image guidance to place the tip of a biopsy system and confirm the direction of delivery to be sure to traverse the target. Flexible scopes are limited in depth of access since they are large (5 mm diameter) and not extremely flexible. They have a working channel of only 2.0 mm so the user is limited in the choice of devices that can be passed through. However, they are steerable, can be locked in place and are substantially stiff to support devices that are prone to buckling (such as compression of a spring needle to traverse a lesion).

One type of conventional flexible bronchoscope is described in U.S. Pat. No. 4,880,015, the disclosure of which is incorporated herein by reference. As shown in FIGS. 1-4, bronchoscope 10 measures 790 mm in length and has two main parts, a working head 14 and an insertion tube 11. The working head contains an eyepiece 15; an ocular lens with a diopter adjusting ring 25; attachments for the suction tubing 24 and a suction valve 21 and for the cold halogen light source 16 and 18; and an access port or biopsy inlet 19, through which various devices and fluids can be passed into the working channel 29 and out the distal end of the bronchoscope. The working head is attached to the insertion tube, which typically measures 580 mm in length and 6.3 mm in diameter. The insertion tube contains fiberoptic bundles (which terminate in the objective lens 30 at the distal tip 12), two light guides 31 and the working channel 29.

The distal end of the bronchoscope has the ability to bend anterior and posterior only, with the exact angle of deflection depending on the instrument used. A common range of bending is from 160 degrees forward to 90 degrees backward, for a total of 250 degrees, as shown at element 13 in FIGS. 3A and 3B. Bending is controlled by the operator by adjusting an angle lock lever 22 and angulation lever 23 on the working head.

Pulmonologists use such bronchoscopes to inspect the interior of the lungs and to perform a variety of procedures. Devices, such as biopsy forceps and brushes, can be passed through the length of the bronchoscope via the working channel into a patient's lungs to obtain tissue samples. For example, a biopsy needle such as that described in U.S. Pat. No. 4,766,906 (the disclosure of which patent is incorporated herein by reference) may be inserted into a patient's lung via the working channel of a flexible bronchoscope. Once the needle is in place at the distal end of the bronchoscope, the pulmonologist can use the needle to, e.g., biopsy a lymph node in the mediastinal space adjacent the bronchus in which the bronchoscope is placed. As described in the '906 patent, the pulmonologist makes a stabbing motion with the bronchoscope and needle to penetrate the bronchial wall and the lymph node. Other examples of biopsy needles used via the working channel of bronchoscopes may be found in U.S. Pat. No. 5,056,529, U.S. Pat. No. 4,532,935 and U.S. Pat. No. 4,702,260, the disclosures of which are incorporated herein by reference.

SUMMARY OF THE INVENTION

The size of the working channel of conventional bronchoscopes limits the size of instruments that may be passed down the working channel to view, biopsy or treat a patient's lung at the distal end of the bronchoscope. For example, current needle biopsy devices for sampling in or through the lung must fit through the 2.0 mm diameter channel of conventional bronchoscopes. In addition, because the bronchoscopes working channel is being used to deliver the biopsy needle, the scope cannot be simultaneously used for other purposes, such as fixation of the target tissue. The present invention provides an access accessory for use with a bronchoscope that overcomes the size limitations of the bronchoscope's working channel.

Accordingly, in one embodiment, the present invention provides a lung access assembly. The assembly comprises: (a) an imaging device having a proximal end, a distal end, said distal end being adapted to be placed within a subject's lung and said proximal end being adapted to be located outside of said subject's lung; and (b) a guide element being operably connected to said distal end of said imaging device to direct delivery of an instrument outside said imaging device to said subject's lung. Kits comprising the subject lung access assembly are also contemplated.

In a separate embodiment, the present invention provides a method of using the subject lung access assembly. In particular, included in this embodiment is a method of providing a guided access to a subject's lung or surrounding tissue. The method involves positioning the subject lung access assembly into an inner part of the lung or surrounding tissue, and controlling the guide element contained in the assembly to effect a guided access with an instrument located outside of the imaging device of the assembly, or outside the working channel if the imaging device contains one.

Further provided by the present invention is a method of performing a treatment or diagnosis of a targeted site in a subject's lung or surrounding tissue of the lung. The method involves the steps of (a) delivering the subject lung access assembly into an inner part of the lung or surrounding tissue, wherein said assembly comprises (i) an imaging device comprising a working channel; (b) controlling a guide element under the view of the imaging device of the assembly; (c) inflating a balloon operably connected to the guide element to fixate an instrument to be delivered to a target site in the lung or surrounding tissue; and (d) performing the desired treatment to or diagnosis at the fixated targeted site with the instrument.

In some embodiments, the access accessory is reverse loaded into a bronchoscope's working channel before the bronchoscope is inserted into the patient. The access accessory has one or more elements (guide wires, cannulas, etc.) attached to its distal end so that the elements are pulled down the throat and into the bronchi along with the bronchoscope.

After bronchoscope placement, the physician can introduce devices such as large visualization light fiber bundles, scrapers, instruments to manipulate sutures or suture needles, laser light fibers, light canes, light tubes, biopsy location marker delivery systems, tumor removal instruments, plugs, ultrasound probes, angioscopes, or other devices for performing therapy or modifying the shape or condition of the patient's throat, windpipe, trachea, bronchi, lung, mediastinal region, lymph nodes, and tumors) over the guide wire, through the cannula, etc. These devices can be delivered into the patient's lung with the bronchoscope still in place or with the bronchoscope removed, leaving the access accessory in place. The access accessory can also be used to help control the position of the bronchoscope or other device.

In addition, anatomical features such as the patient's vocal chords by which the bronchoscope must pass on its way into the lungs limit the amount the bronchoscope's diameter may be increased and may prevent the simultaneous delivery of tools along with but exterior to the bronchoscope. The access accessory of the present invention provides a way to overcome these anatomical size limitations by enabling instruments to be delivered exterior of the bronchoscope to the bronchoscope's distal end without having to deliver the instruments simultaneously with or alongside the bronchoscope.

In certain embodiments, the imaging device of the subject assembly is a bronchoscope, and the guide element is a guide wire. More than one guide element can be built into the assembly. Typically, the guide element has a distal end and a proximal end, whereas the distal end is designed to be placed within a subject's body and is connected to said instrument, and the proximal end is located outside of the subject's body so as to direct the delivery of an instrument. In certain embodiments, at least a portion of the guide element is disposed within a working channel of the imaging device. In a preferred aspect, the guide element is located within or traversing a balloon shaft for delivering a balloon to said inner part of the lung or surrounding tissue of the lung. In another preferred aspect, the balloon shaft contains at least one side port to allow passage of the guide element. The guide element can be an integral part of the instrument. The guide element can also be connected to the instrument via a separable attachment device (see, e.g., FIGS. 27A-D). Preferred separable attachment device allows controlled release of the guide element from the instrument when placed inside a subject's lung or surrounding tissue. Such separable attachment device includes but is not limited to a clip, an adhesive, a strap, and a sleeve. Where desired, the separable attachment device may further comprise a working channel.

In some embodiments, the instrument being connected to the guide element is located within or traversing the distal end of a working channel of the imaging device. In some embodiments, the instrument is located outside the imaging device. A variety of instruments can be used in conjunction with the subject assembly. They include but are not limited to instruments that are adapted to perform biopsy, instruments that are adapted to image bodily tissues and/or deliver a pharmaceutical composition to the lung. A preferred instrument comprises a catheter connected to a balloon. Another preferred instrument comprises a needle guide. Where desired, the needle guide may contain a side port to allow passage of the guide element.

Another aspect of the invention pertains to the fixation of target tissue for biopsy. The consistency of lymph node or other tissue biopsied through the lungs can range from fluid to hard rubbery lumps that roll out of the way when pressed with a biopsy needle. The invention therefore provides ways to fix the target tissue prior to biopsy, such as by using the access accessory to deliver and control a fixation device. The invention also enables the delivery of larger biopsy needles in order to extract larger tissue samples than prior lung biopsy systems permit.

Accordingly, the present invention provides a method of fixating a lung tissue for treatment or diagnosis. This method involves (a) delivering a lung access assembly into an inner part of the lung or surrounding tissue, wherein said assembly comprises (i) an imaging device comprising a working channel; and (ii) a guide element observable under a view of said imaging device, wherein at least a portion of said guide element is disposed inside said working channel to effect a guided access to said inner part or surrounding tissue of the lung with a plurality of fixation instruments, and wherein at least one fixation instrument of said plurality is operatively connected to a guide element; and (b) contacting said plurality of fixation instruments to fixate said lung tissue. In one aspect of this embodiment, the fixation instruments comprise needle guides carried therein a plurality of needles. Preferred needles are covered by an expandable sleeve.

The present invention further provides a space-making device for accessing a bodily organ or tissue. The device comprises the following components: (a) an elongated access device having a distal end, a proximal end, and a lumen therethrough, said device carrying a delivery element extendable through said lumen; (b) an open-ended and extendable sleeve surrounding said distal end of said elongated access device, wherein said extendable sleeve is designed to effect expansion of working space for accessing said bodily organ or tissue with said delivery element.

Also included in the present invention is a method of providing working space for accessing said bodily organ or tissue in a subject. The method involves (a) positioning a space-making device into said bodily organ or tissue of said subject, wherein said device comprises (i) an elongated access device having a distal end, a proximal end, and a lumen therethrough, said device carrying a delivery element extendable through said lumen; and (ii) an open-ended and extendable sleeve surrounding said distal end of said elongated access device; and (b) expending said extendable sleeve to effect expansion of working space for accessing said bodily organ or tissue with said delivery element.

In some aspects of this embodiment, the sleeve is radially extendable. In other aspects, the sleeve comprises at least one wing structure to facilitate spreading apart anatomical features at said bodily organ or tissue.

Other advantages of the invention will be apparent from the description of the specific embodiments below.

BRIEF DESCRIPTION OF THE DRAWINGS:

FIG. 20 shows a bronchoscope system in which a balloon catheter, side port needle guide, biopsy needle and center wire are all disposed within the bronchoscope's working channel;

FIGS. 23A-B, 24A-B and 25 show other embodiments of space-making devices that can be delivered via a bronchoscope system to provide working space for a procedure;

DETAILED DESCRIPTION OF THE PREFERRED EMBODIMENTS

Figure 1:
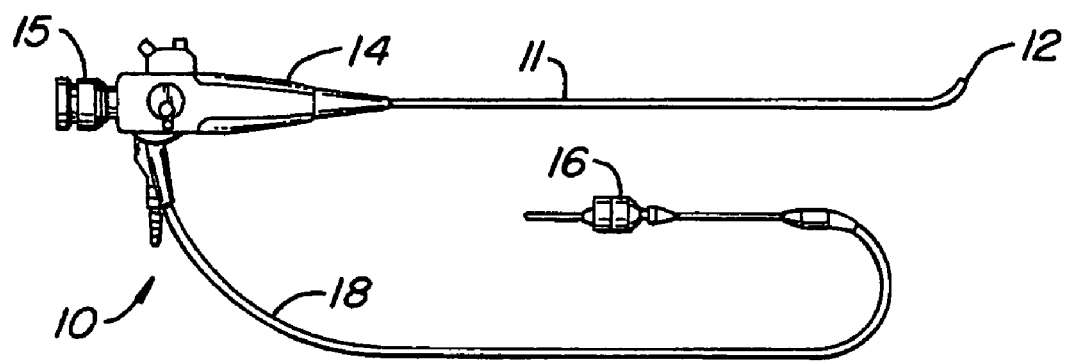
FIGS. 1, 2, 3A-B and 4 show a bronchoscope.
Figure 2:
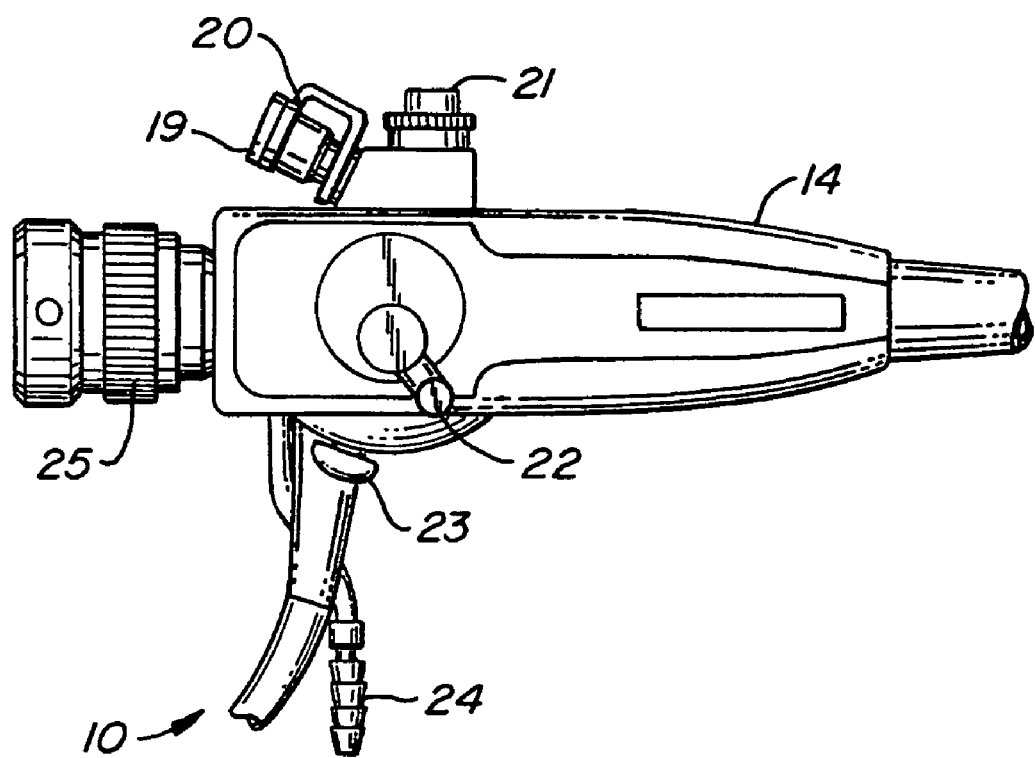
Figure 3A:
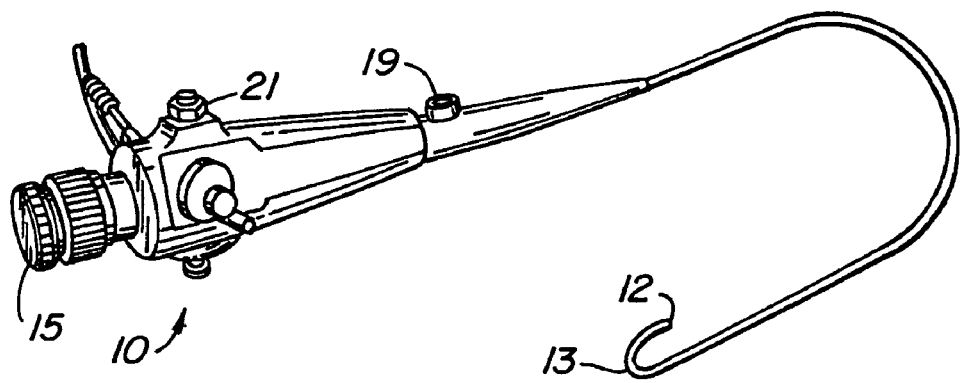
Figure 3B:
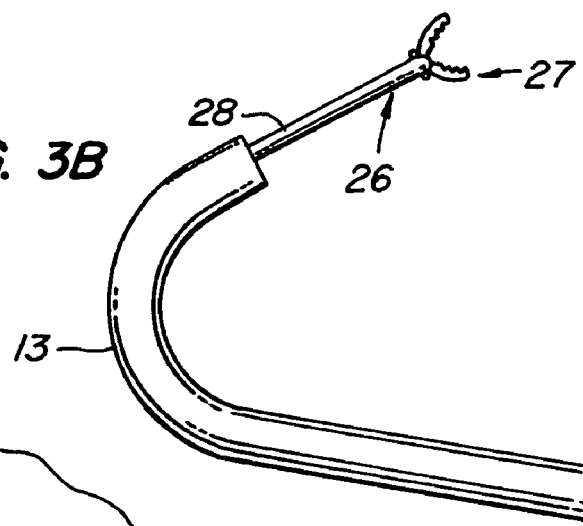
Figure 4:
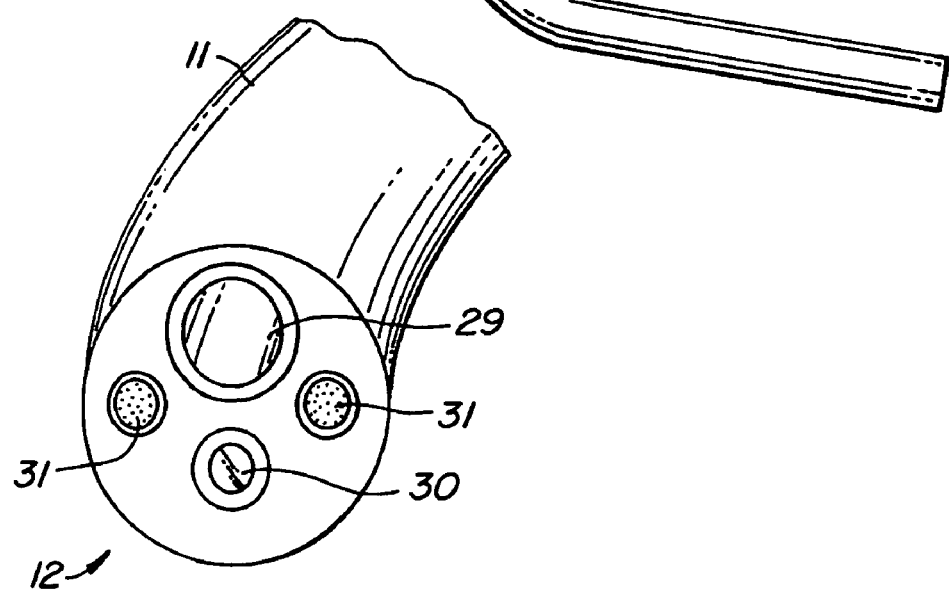
Figure 5:
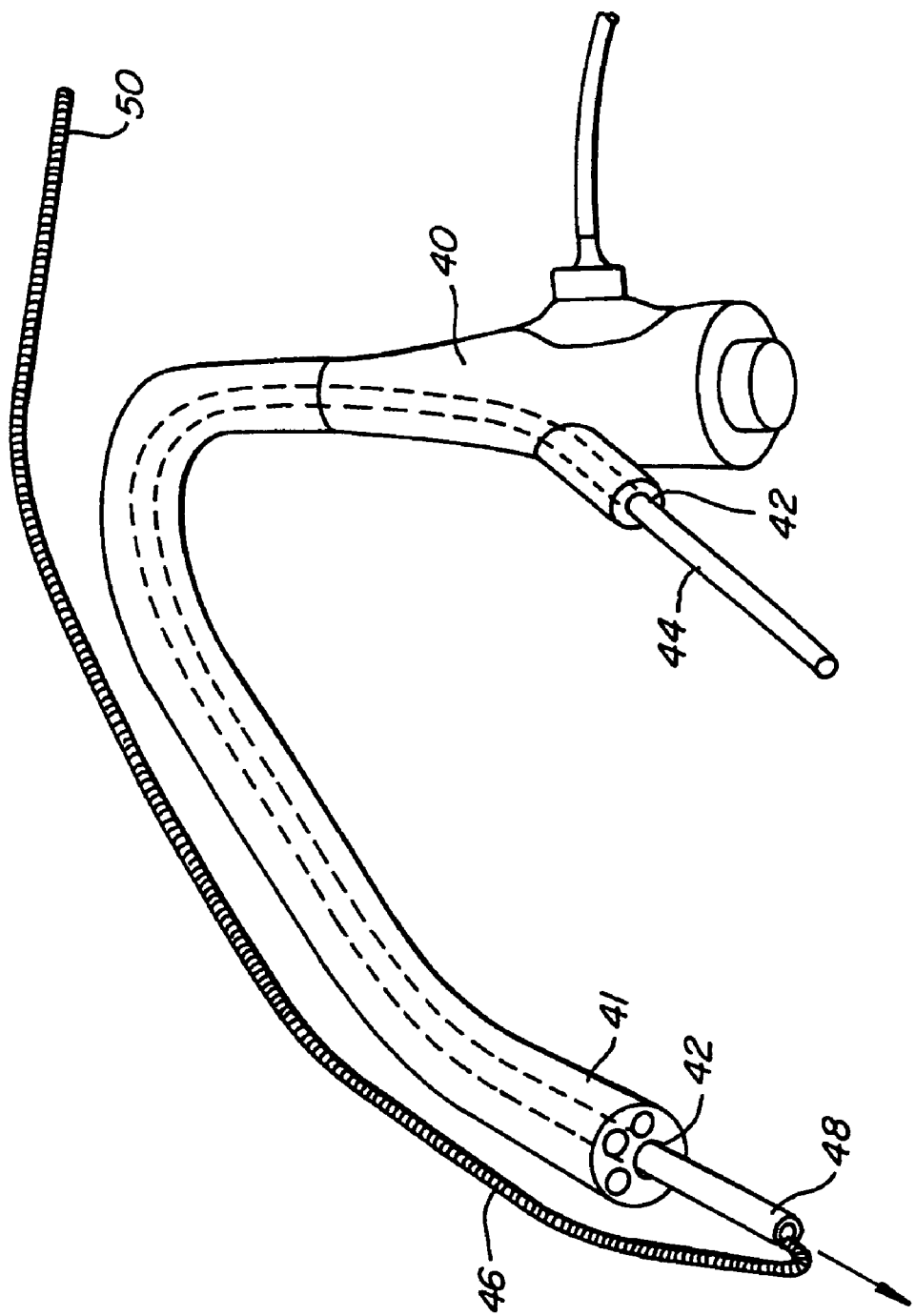
FIG. 5 shows a flexible bronchoscope with a working channel into which a needle guide has been inserted.

FIG. 5 shows a flexible bronchoscope 40 with a working channel 42 into which a needle guide 44 has been inserted. Prior to inserting bronchoscope 40 into a patient, a an access accessory such as guide wire 46 is inserted into the distal end 48 of needle guide 44. Guide wire 46 is bent around so that a proximal end 50 lies along the length of bronchoscope 40. When bronchoscope 40 is inserted into a patient's lungs, the proximal end 50 of guide wire 46 will remain outside of the patient. Guide wire 46 can then be used to deliver diagnostic, therapy or biopsy tools to the distal end of bronchoscope 40 without having to pass such tools through working channel 42. Such tools can be delivered either simultaneously alongside the bronchoscope or after the bronchoscope has been placed at the selected site within the patient's lung.

The guide wire 46 can also be used to position and steer the distal end 41 of the bronchoscope. Pulling guide wire 46 in a proximal direction will cause the needle guide 44 and distal end 41 of bronchoscope 40 to bend in that direction, thereby enhancing the user's control of the distal end of the bronchoscope.

In an alternative embodiment, the guide wire can be attached to or made integral with the needle guide.

Figure 6:
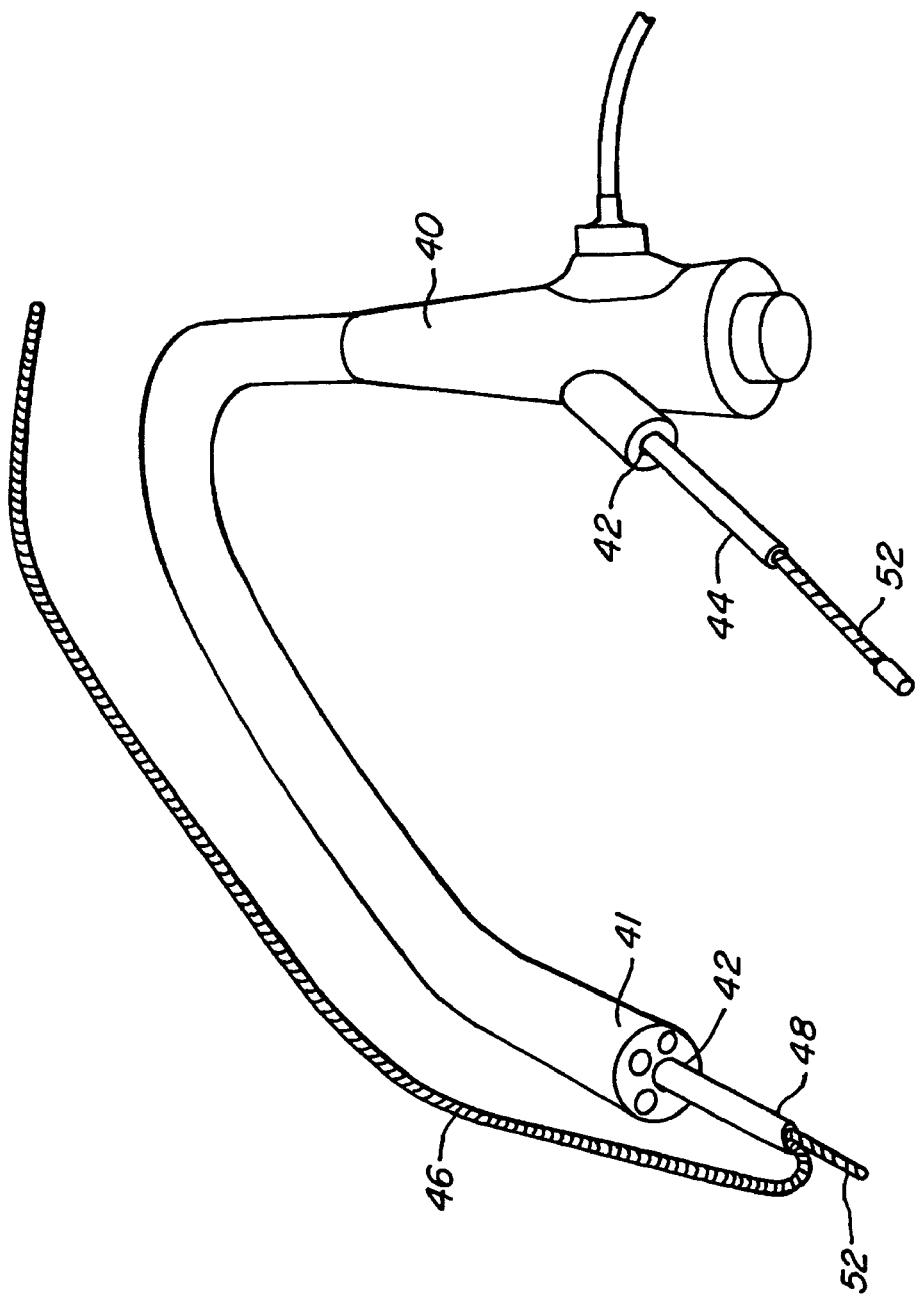
FIG. 6 shows the use of a blunt dilator with the bronchoscope, needle guide and guide wire arrangement of FIG. 5.

FIG. 6 shows the use of a blunt dilator 52 with the bronchoscope 40, needle guide 44 and guide wire 46 arrangement of FIG. 5. Dilator 52 can be used to help advance the system without causing trauma to the wall of the bronchi or other lung passage.

Figures 7A, 7B:
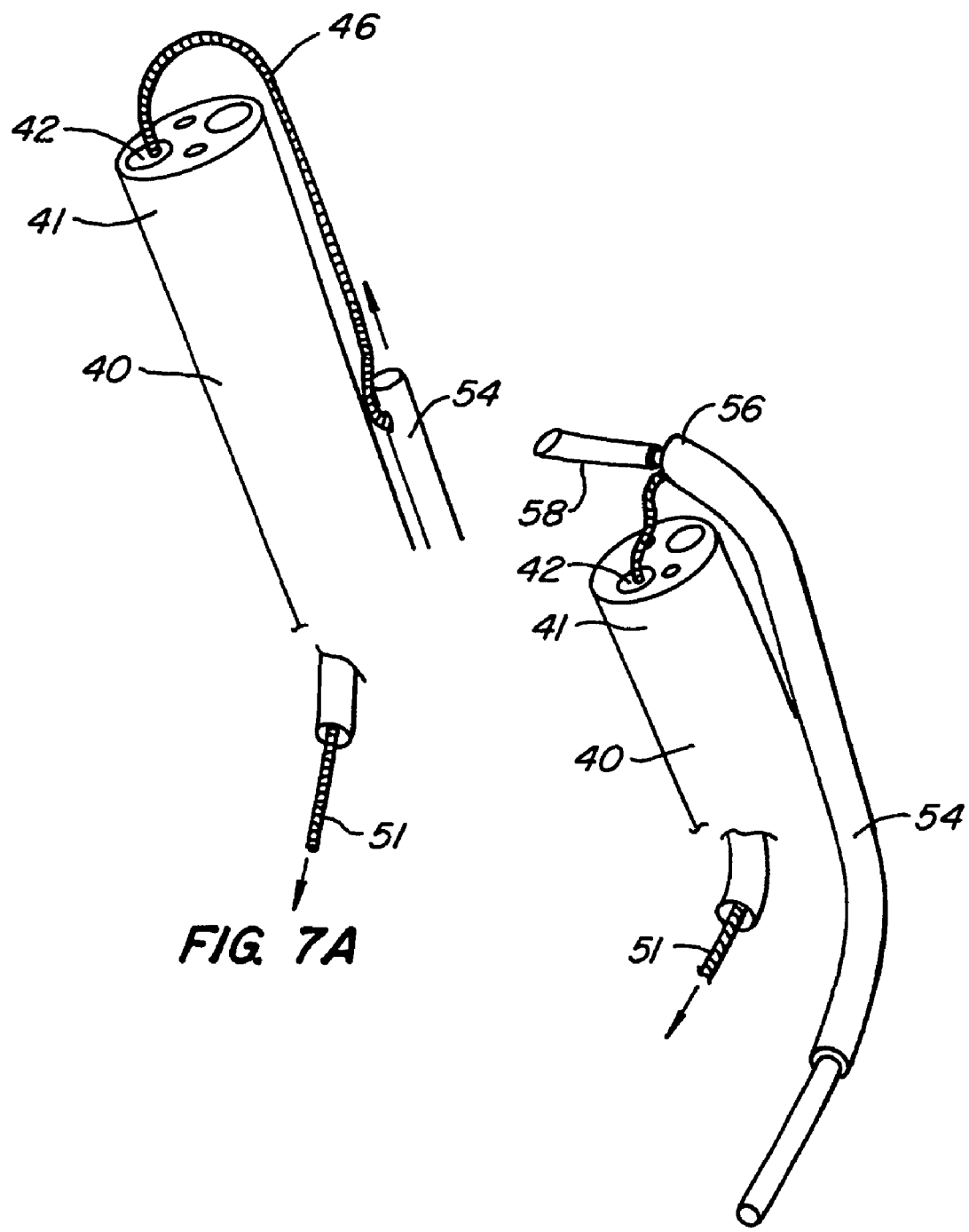
FIGS. 7A-B and 8 show an embodiment of the invention that omits the use of a needle guide within the working channel of the bronchoscope.
Figure 8:
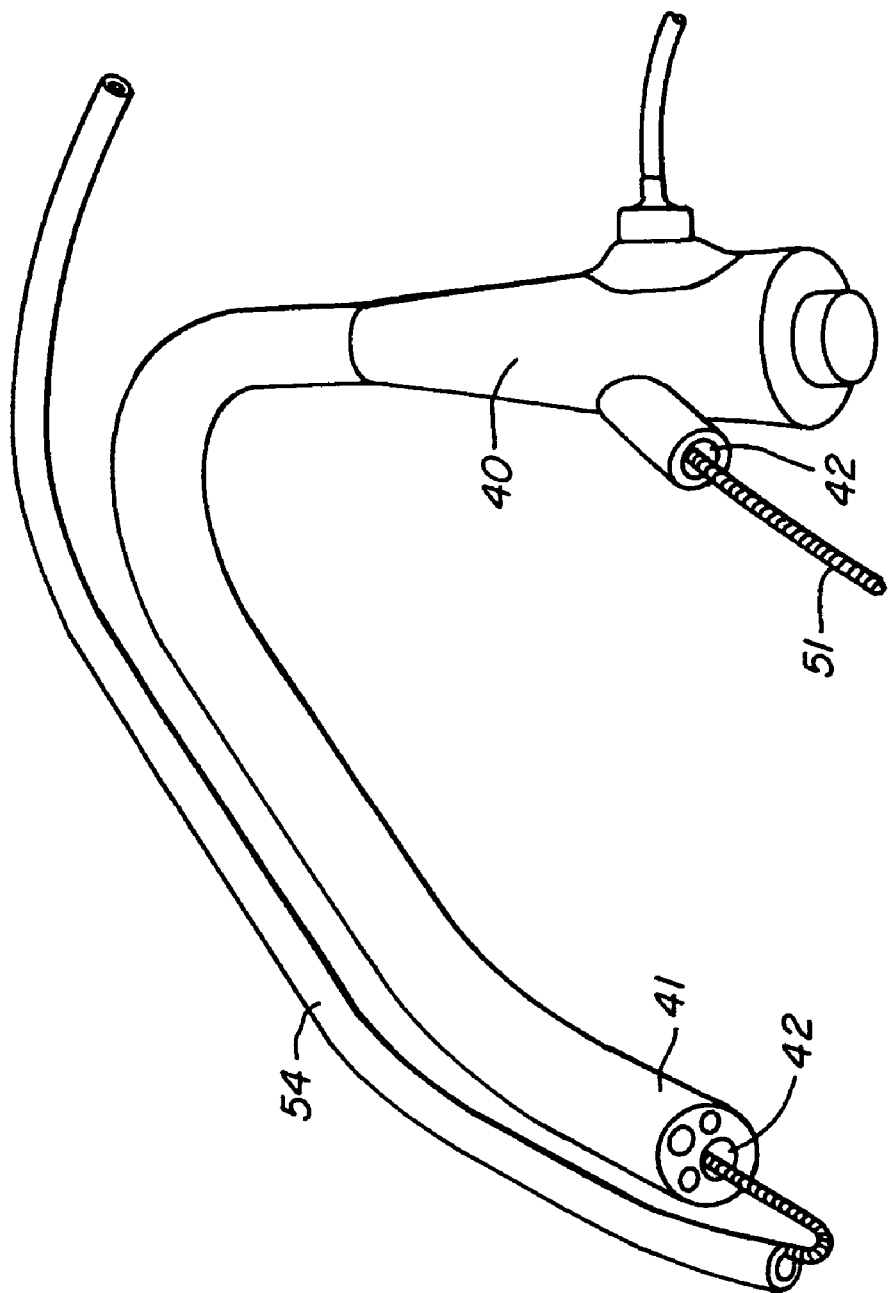
Figure 9:
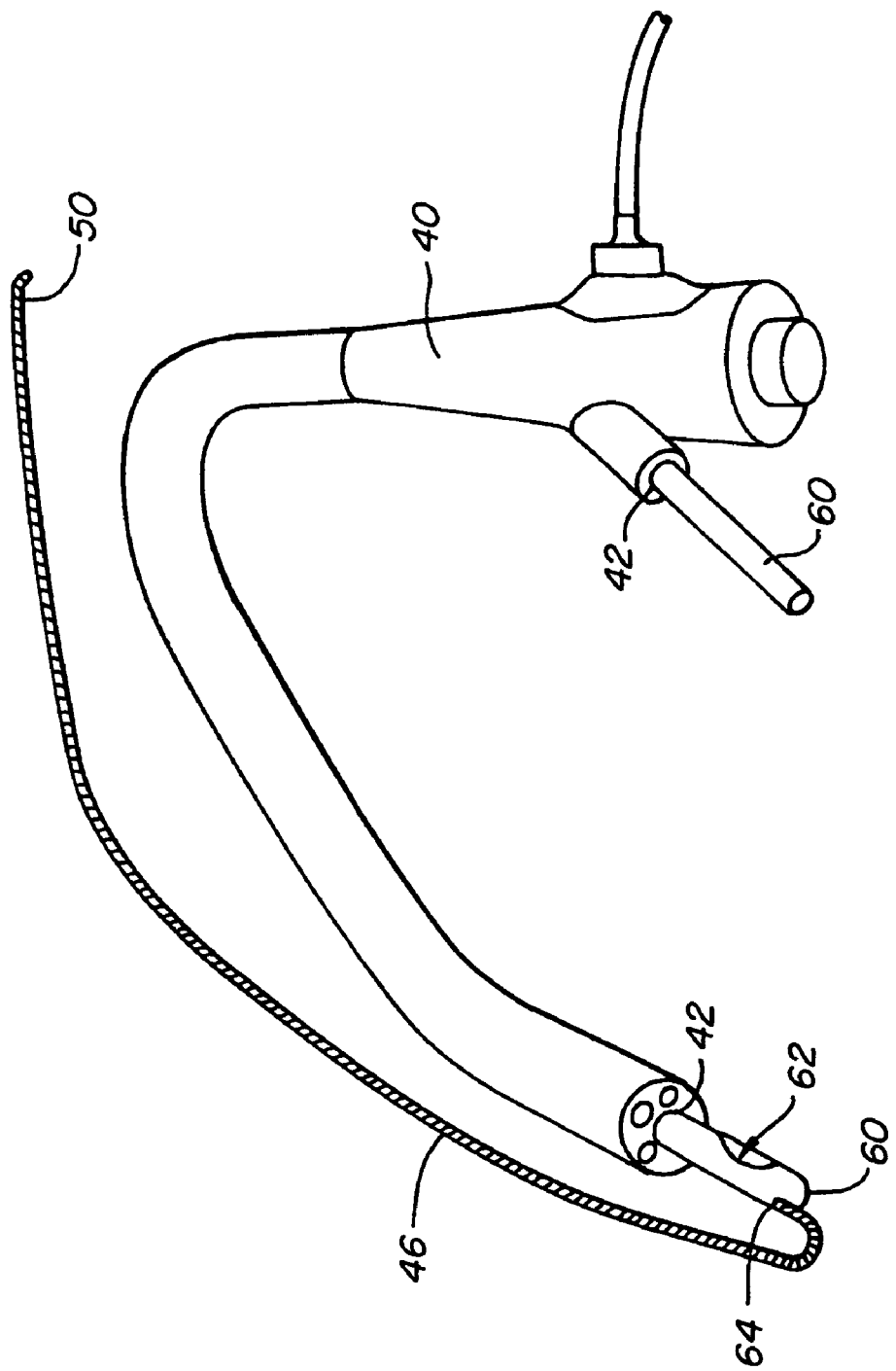
FIGS. 9-12 show a bronchoscope and guide wire arrangement in which a blunt tipped needle guide with a side port is disposed in the working channel of bronchoscope.

FIGS. 7 and 8 show an embodiment of the invention that omits the use of a needle guide within the working channel 42 of the bronchoscope 40. In this embodiment, guide wire 46 is placed in the working channel 42 at the distal end 41 of the bronchoscope so that one end 51 extends proximally through the working channel and the other end (not shown) extends proximally outside the bronchoscope along its length to the exterior of the patient. When the bronchoscope is inserted into the patient's lung, guide wire 46 can be used to deliver tools to the treatment site. In the example shown in FIGS. 7A and 7B, guide wire 46 is being used to deliver a needle guide 54 to a biopsy site, either by pushing needle guide 54 distally along guide wire 46, withdrawing proximal guide wire end 51 proximally while needle guide 54 is on the exterior portion of guide wire 46, or a combination of both actions. When the distal end 56 of needle guide is at the distal end 41 of the bronchoscope, the needle guide's distal end 56 follows the curve of guide wire 46 to bend toward the biopsy site. Proximal tension on guide wire 46 can be used to control the amount of needle guide bending. A flexible biopsy needle 58 within needle guide 54 may then be used to penetrate the bronchial wall to take the tissue sample.

FIGS. 9-12 show a bronchoscope and guide wire arrangement in which a blunt tipped needle guide 60 with a side port 62 is disposed in working channel 42 of bronchoscope 40. Guide wire 46 is fixed in a guide wire port 64 at the distal end of needle guide 60 prior to inserting bronchoscope 40 into the patient so that guide wire 46 extends along the length of bronchoscope 40 to place a proximal end 50 of guide wire 46 outside the patient. Guide wire 46 may be used to rotate and/or bend needle guide 60 to orient side port 62 as desired. As in the other embodiments, after insertion of bronchoscope 40 into a patient's lung, guide wire 46 may be used to deliver tools (such as a grasper, light source, tumor fixator, forceps) to the distal end of bronchoscope without having to pass through the bronchoscope's limited size working channel. Other delivery tools are described in applicant's copending U.S. Patent Application Publication Ser. No. 11/153,235, the contents of which are incorporated herein by reference in their entirety.

Figure 10:
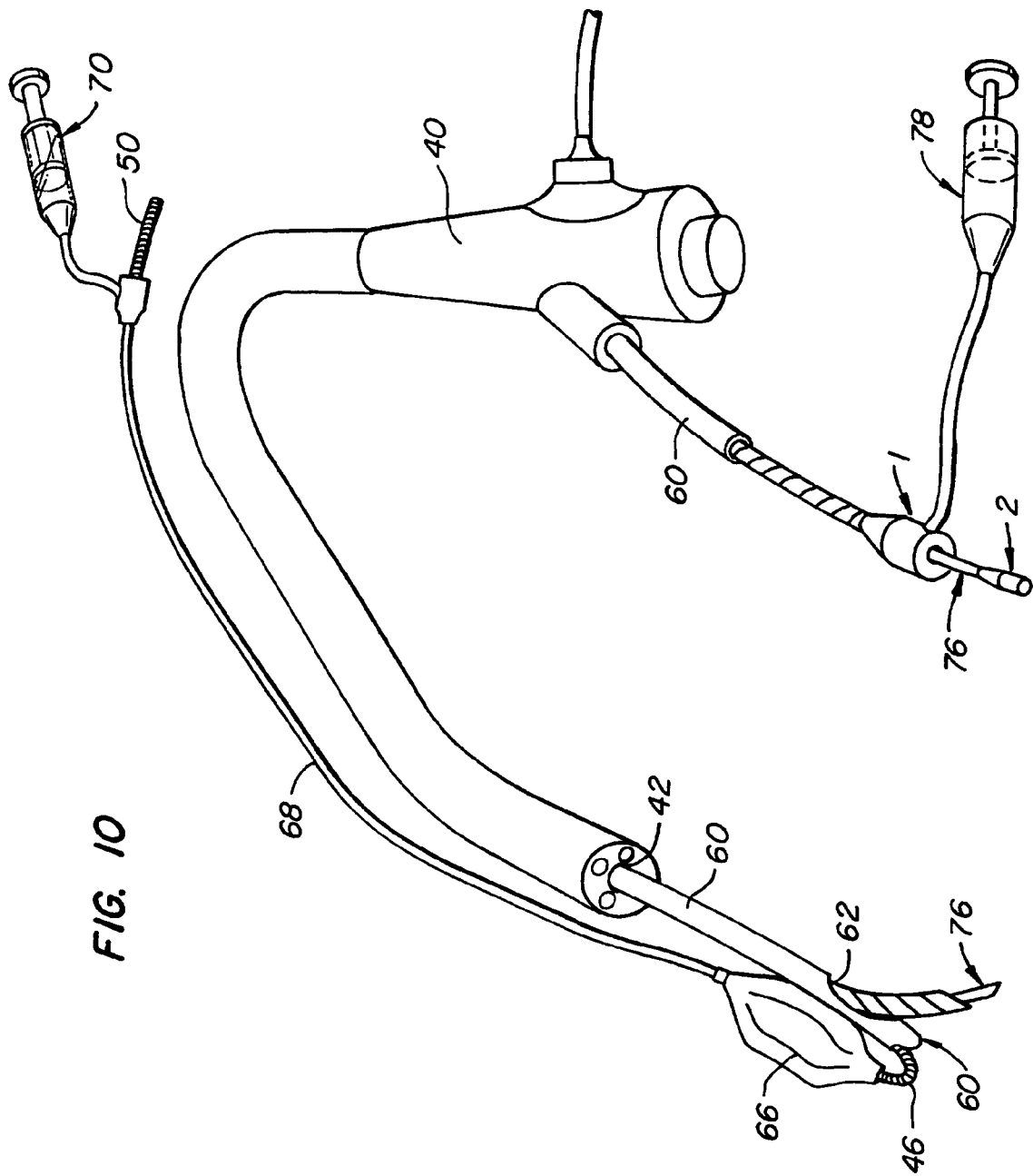
Figure 11:
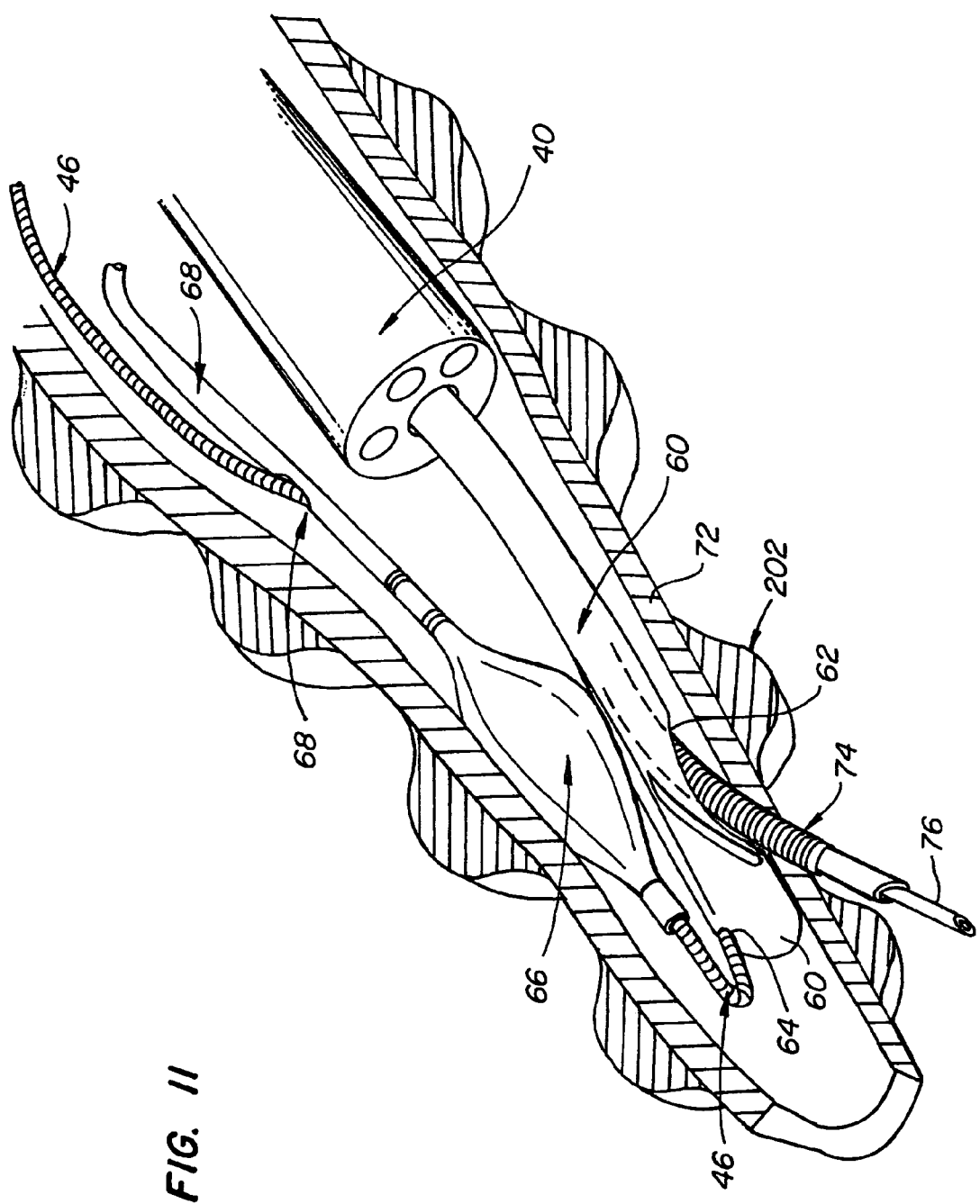
Figure 12:
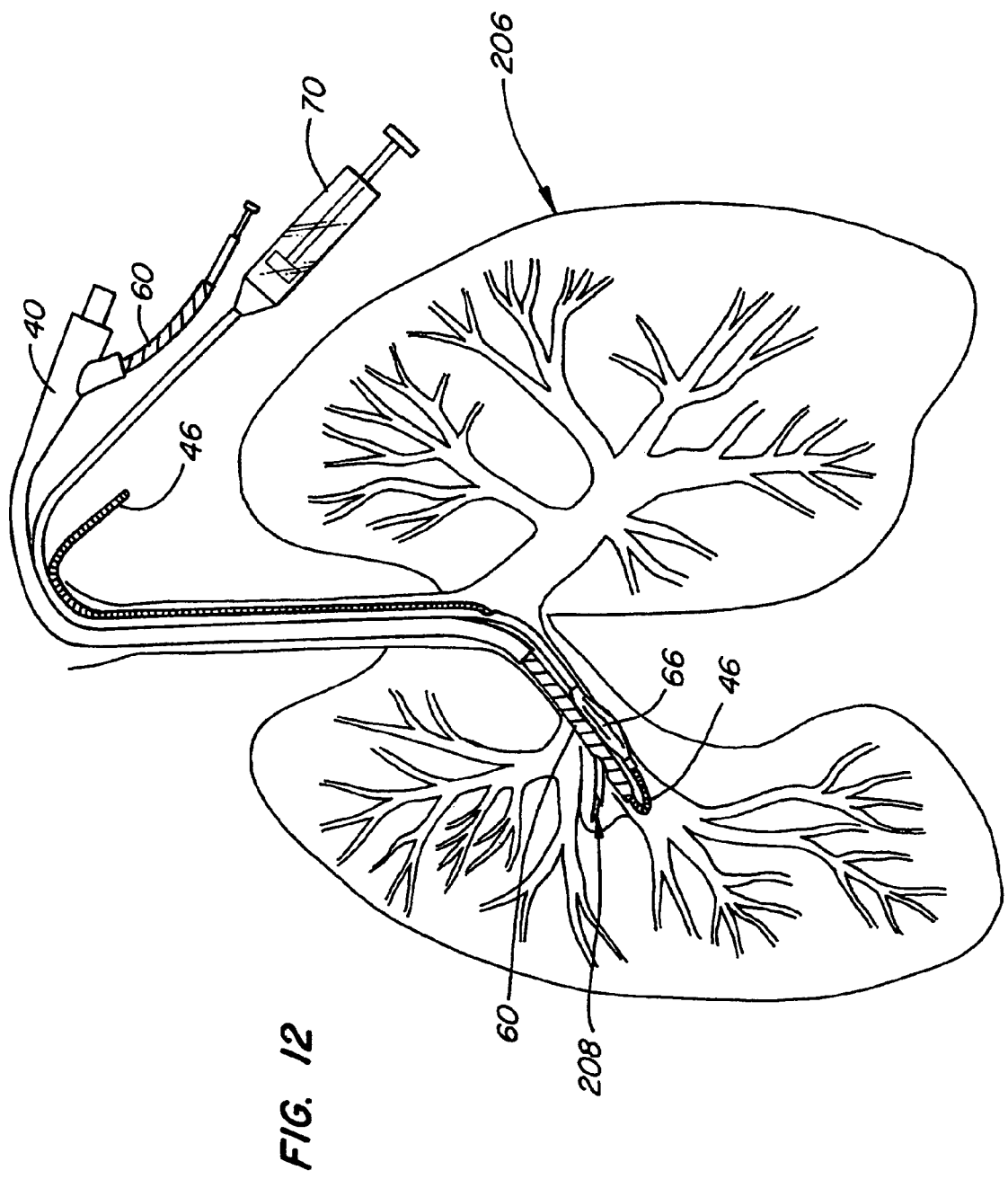

For example, FIGS. 10-12 show the use of the bronchoscope system to deliver a balloon 66 to a biopsy site. The catheter 68 communicating with balloon 66 may be coaxial with guide wire 46 as shown in FIG. 10; alternatively, guide wire 46 may exit the balloon's shaft 66 via a side port 69 as shown in FIG. 11. The balloon's inflator 70 is disposed outside of the patient at the proximal end 50 of guide wire 46. After using guide wire 46 to orient side port 62, balloon 66 is inflated to move side port 62 toward or against the bronchial wall 72 at the biopsy site and to hold the distal end 60 of the needle guide in this position. A biopsy needle 74 and center wire 76 may then be advanced through needle guide 60 and through side port 64 through the bronchial wall 72 into the biopsy site. The center wire 76 may be used to fix the suspected tumor in place as an aspirating syringe 78 is used to draw a tissue sample into the core biopsy needle 74. After taking the tissue sample, the needle and center wire are withdrawn, and balloon 66 may be deflated.

Figure 13:
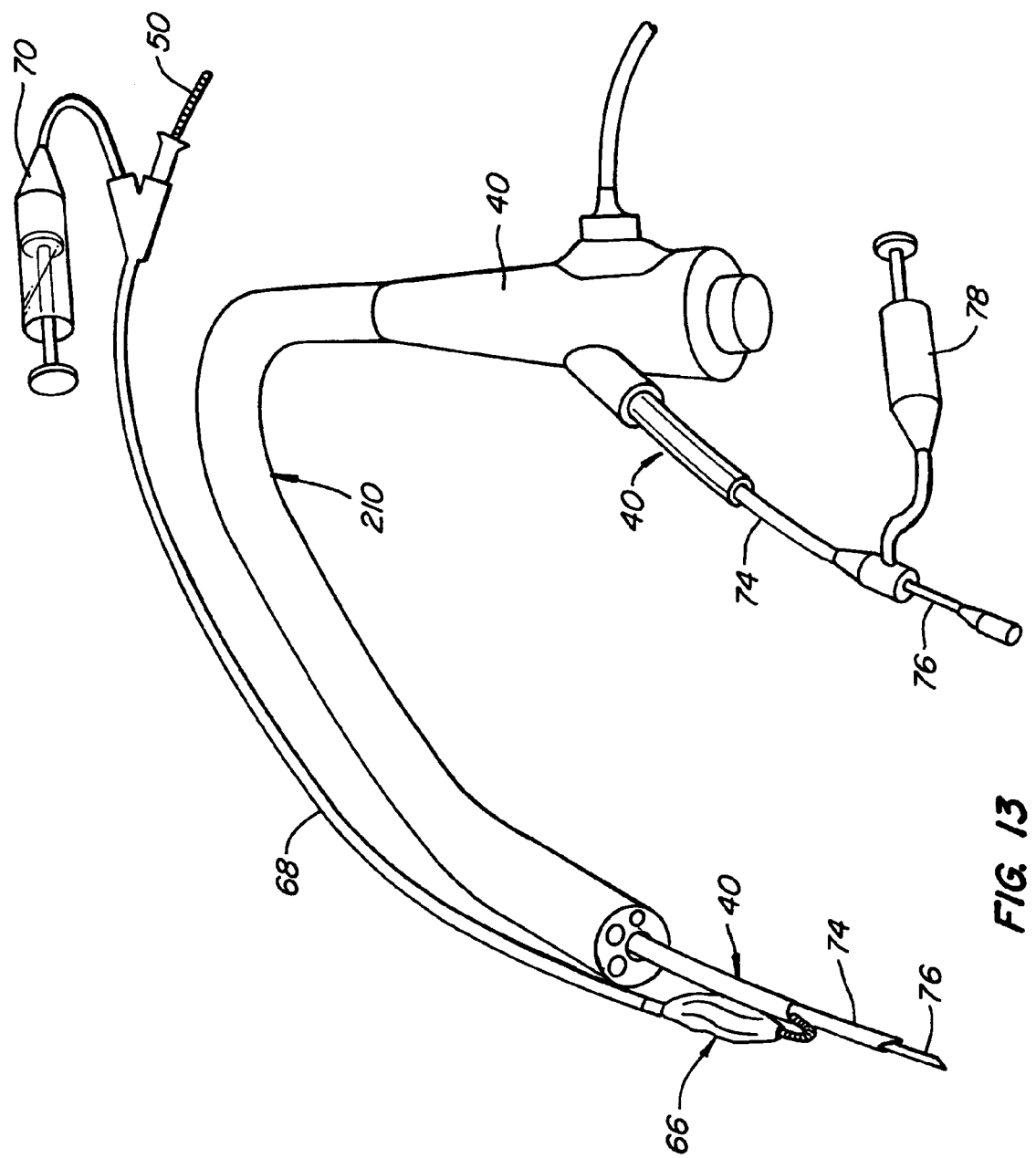
FIG. 13 shows a bronchoscope system similar to that of FIGS. 9-12 in which the side port needle is replaced with a straight channel needle guide.

FIG. 13 shows a bronchoscope system similar to that of FIGS. 9-12. The system of FIG. 13, however, replaces the side port needle guide of FIGS. 9-12 with a straight channel needle guide 44. Like the system of FIGS. 9-12, balloon 66 may be used to orient and support needle guide 44 prior to and during the biopsy procedure.

Figure 14:
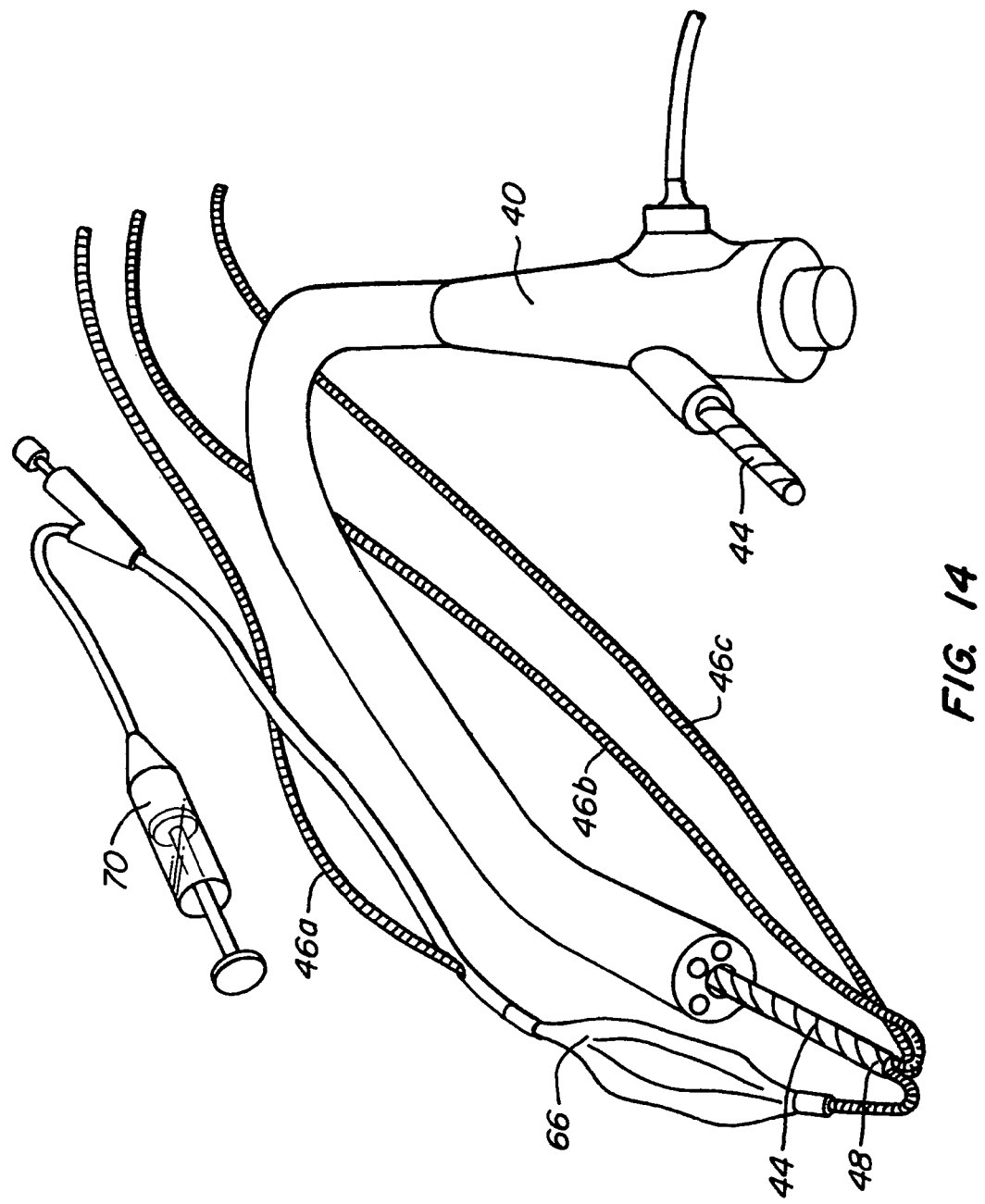
FIG. 14 shows a bronchoscope system in which multiple guide wires are disposed in a needle guide 44.

FIG. 14 shows a bronchoscope system in which multiple guide wires 46a, 46b, and 46c are disposed in a needle guide 44 extending through the working channel of bronchoscope 40. As in the other embodiments, one end of each of the guide wires is inserted into the distal end 48 of the needle guide prior to insertion of the bronchoscope into the patient so that the guide wires extend along the length of bronchoscope 40 to place their other ends 50a, 50b and 50c outside of the patient. Tools such as side port balloon 66 may be delivered along the guide wires to the distal end of bronchoscope 40 without using the bronchoscope's working channel.

In an alternative embodiment, the guide wire can be attached to or made integral with the needle guide.

Figure 15:
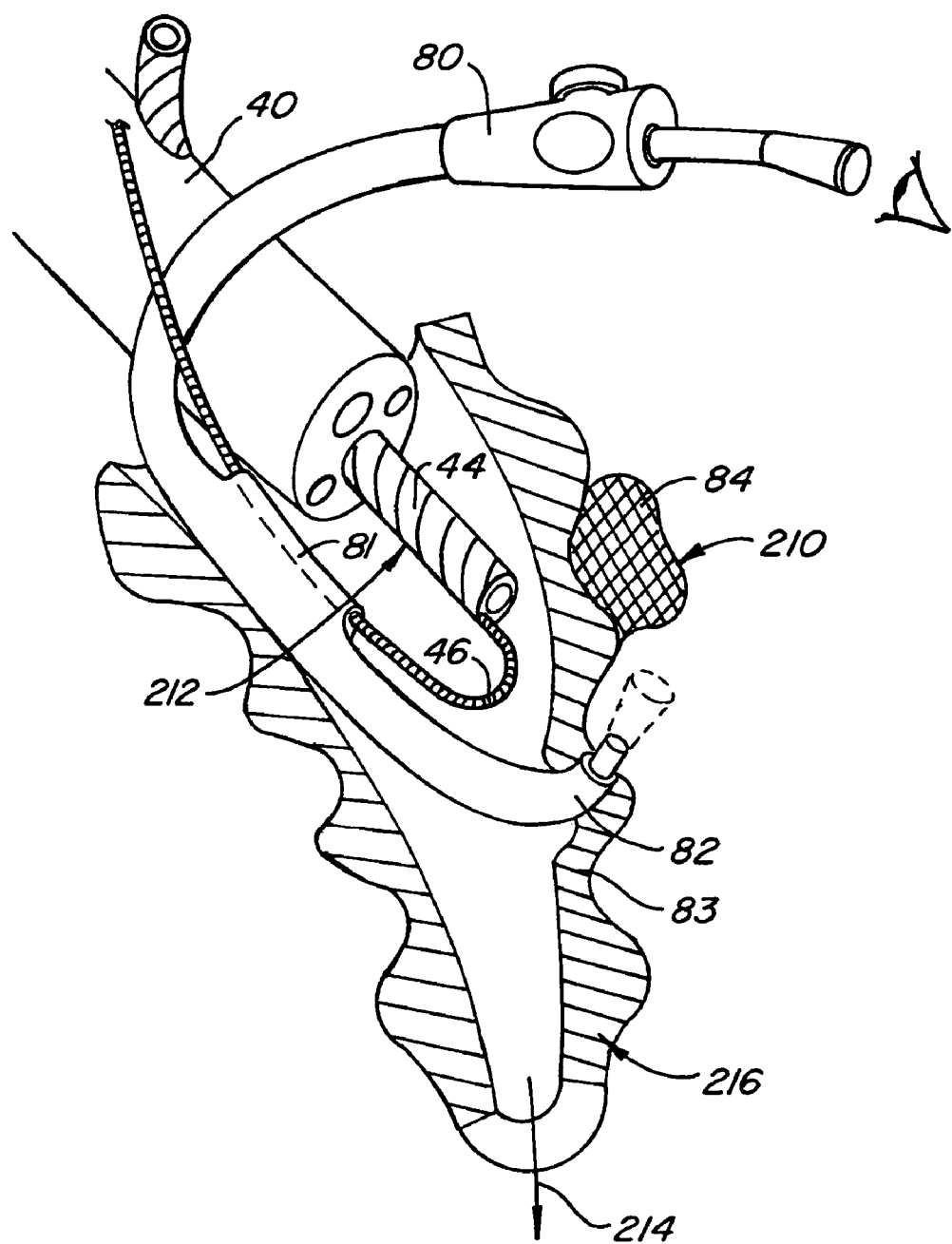
FIG. 15 shows the use of a guide wire bronchoscope system similar to that of FIG. 5 to deliver a steerable scope.

FIG. 15 shows the use of a guide wire bronchoscope system similar to that of FIG. 5 to deliver a steerable scope and/or camera 80 to a biopsy site via a rail 81 running along guide wire 46. The directable distal end 82 of scope 80 may penetrate the bronchial wall 83 adjacent the suspected tumor or lymph node 84 to view the tissue to be biopsied. A biopsy needle may be delivered to the biopsy site via needle guide 44. The scope's distal end 82 may emit a guide signal (EMF, light, magnetic, sound, radio) to guide the biopsy needle into the suspected tumor or lymph node 84.

Figure 16:
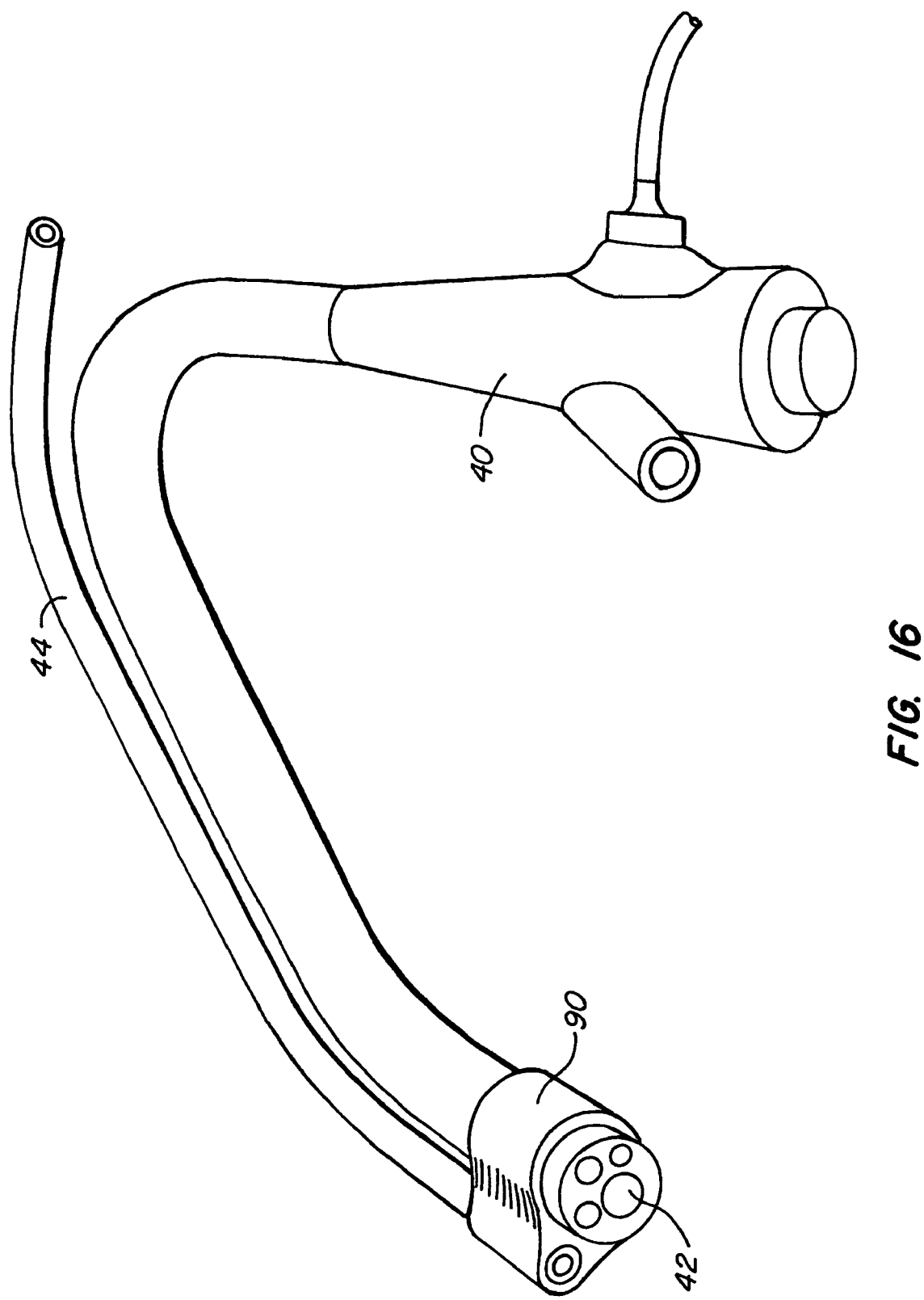
FIGS. 16 and 17 show a needle guide attached to the distal end of the bronchoscope so that biopsy needles or other instruments may be delivered to a treatment site.
Figure 17:
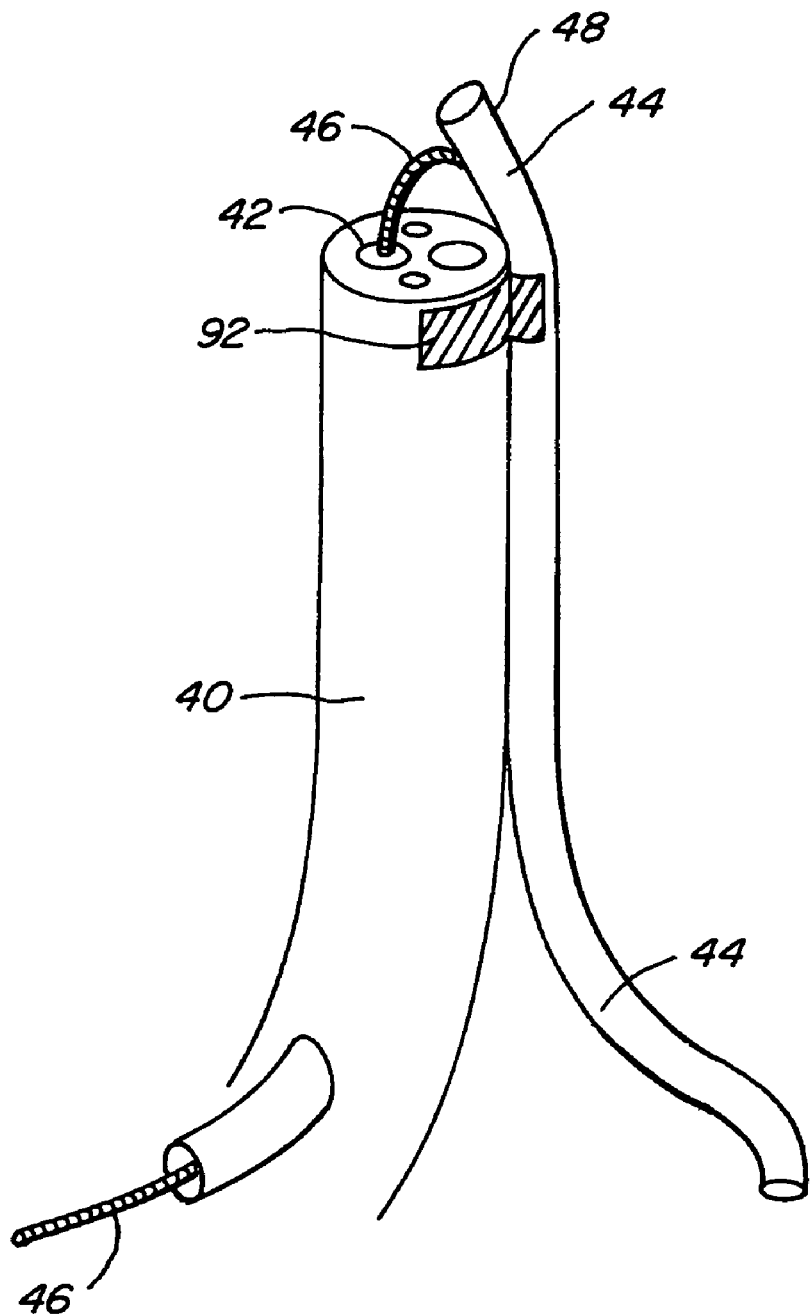

In FIGS. 16 and 17, a needle guide 44 is attached to the distal end 41 of bronchoscope 40 so that biopsy needles or other instruments may be delivered to a treatment site via the guide 44 outside of the bronchoscope's working channel 42. In FIG. 16, needle guide 44 is attached to bronchoscope by a nose clip 90 or other attachment mechanism such as a strap, glue, etc.

FIG. 17 shows the use of a clip, hinge or adhesive 92 to create an articulating connection between the bronchoscope 40 and the needle guide 44. A guide wire 46 extends through the bronchoscope's working channel 42 to the exterior of the patient and also through a side port (not shown) in the needle guide, as in earlier embodiments. The bronchoscope and needle guide are inserted into the lung simultaneously as in the other embodiments, and the guide wire 46 may be used to move, position and hold the distal end 48 of needle guide 44. This arrangement combines the flexibility and maneuverability of the needle guide with the longitudinal stiffness of the bronchoscope.

Figure 18:
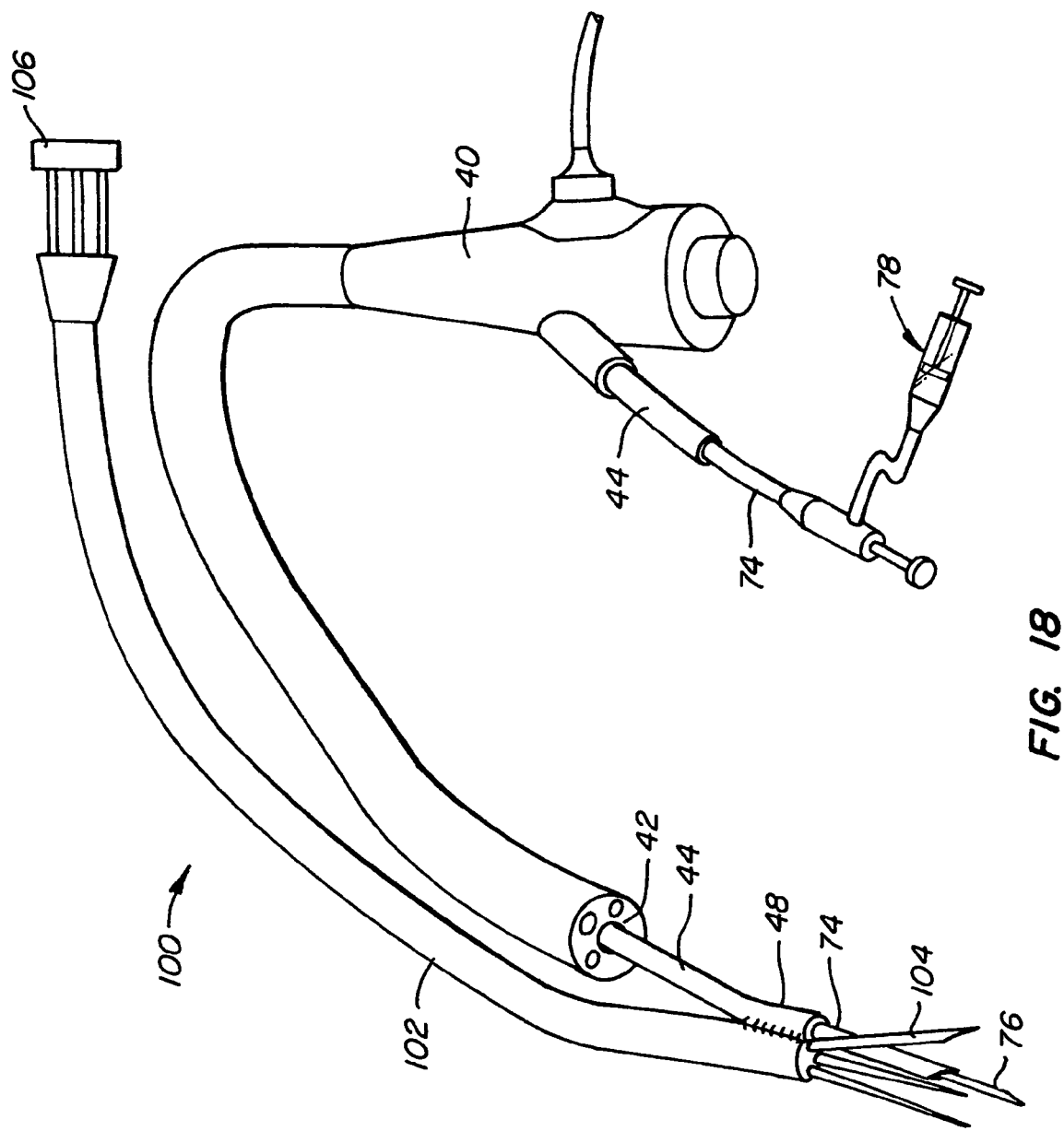
FIG. 18 shows a needle guide attached to a tumor fixation device.

In FIG. 18, a needle guide 44 is sewed together or otherwise attached to a tumor fixation device 100. Needle guide 44 is inserted into the working channel 42 at the bronchoscope's distal end, and the shaft 102 of tumor fixation device 100 extends along the bronchoscope's length. When the bronchoscope is inserted into the patient's lung, one or more fixation needles 104 are at a biopsy site at the bronchoscope's distal end, and a control mechanism 106 is at the device's proximal end outside the patient. Operation of control mechanism 106 inserts needles 104 in and around the tissue to be biopsied. A biopsy needle 74 and center wire 76 may then be used as described above to take a tissue sample.

Figure 19:
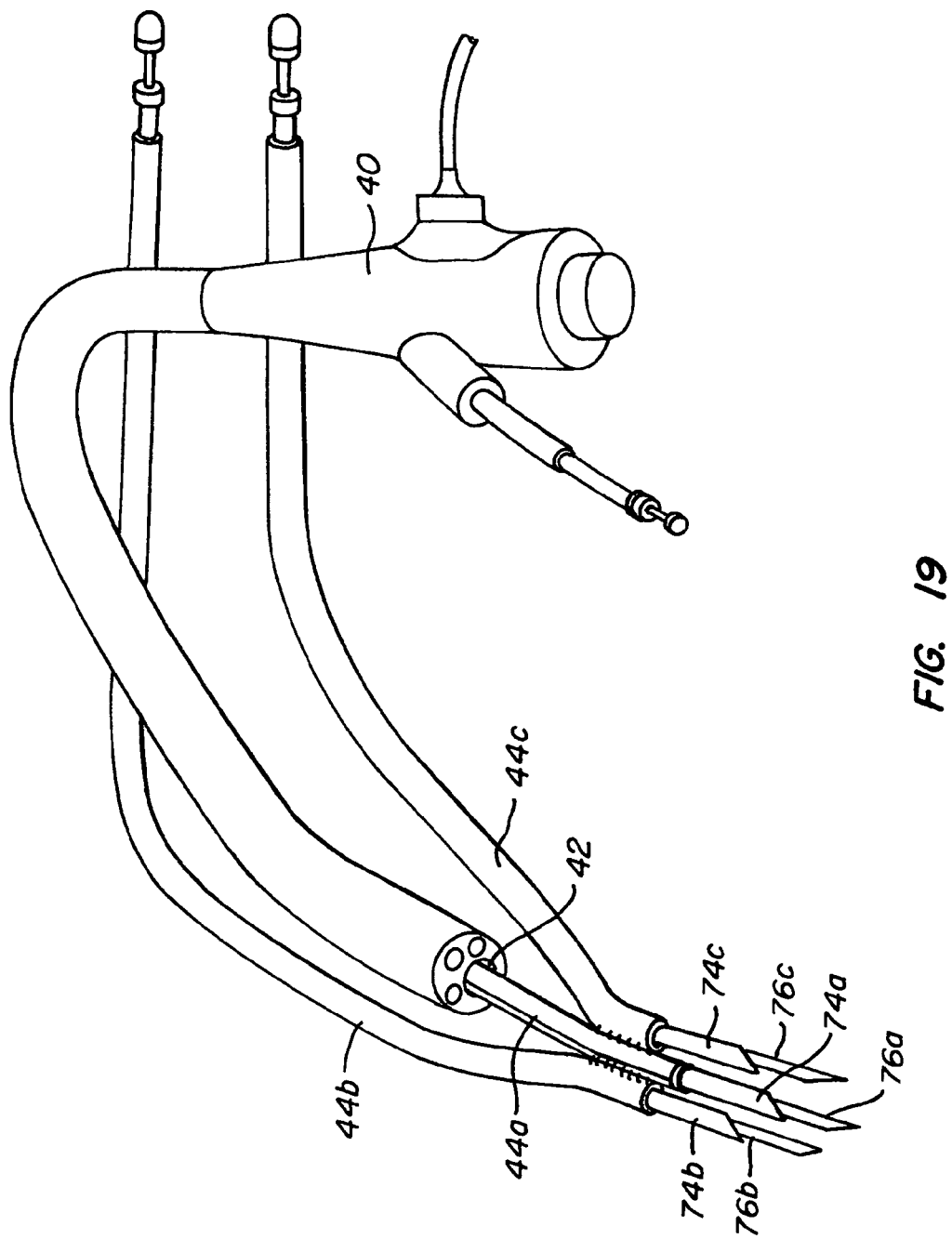
FIG. 19 shows a bronchoscope system with several biopsy needle mechanisms.

FIG. 19 shows a bronchoscope system with several biopsy needle mechanisms. Primary needle guide 44a is disposed in the distal end of working channel 42 of bronchoscope 40 prior to insertion of bronchoscope 40 into the patient's lung. The distal ends of secondary needle guides 44b and 44c are attached to the distal end of primary needle guide 44a by sewing or other means. Each needle guide has center wires and biopsy needles, as shown, which may be operated in a known manner to take tissue samples.

FIG. 20 shows a bronchoscope system in which a balloon catheter 110, side port needle guide 60, biopsy needle 74 and center wire 76 are all disposed within the bronchoscope's working channel. Balloon 10 is disposed opposite to the side port 62 of needle guide 60. Syringe 70 may be used to inflate balloon 110 via balloon shaft 112 to push side port 62 against the bronchial wall so that needle 74 and center wire 76 may be pushed firmly into suspected tumor 84.

Figure 21A:
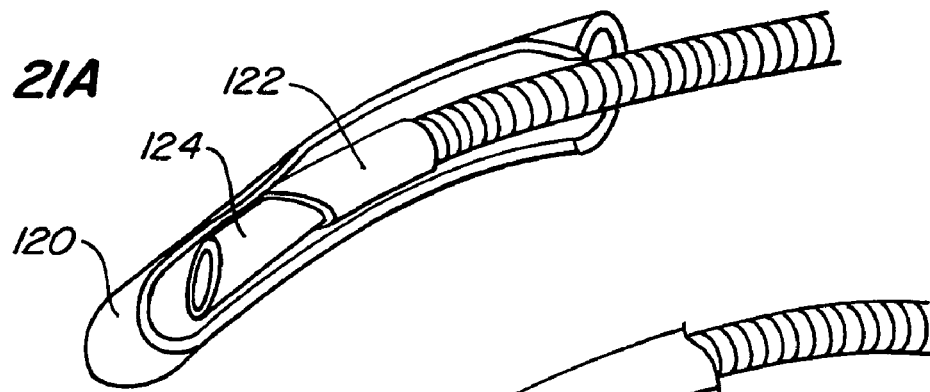
FIGS. 21a-b shows a biopsy needle for use with bronchoscope systems described herein.
Figure 21B:
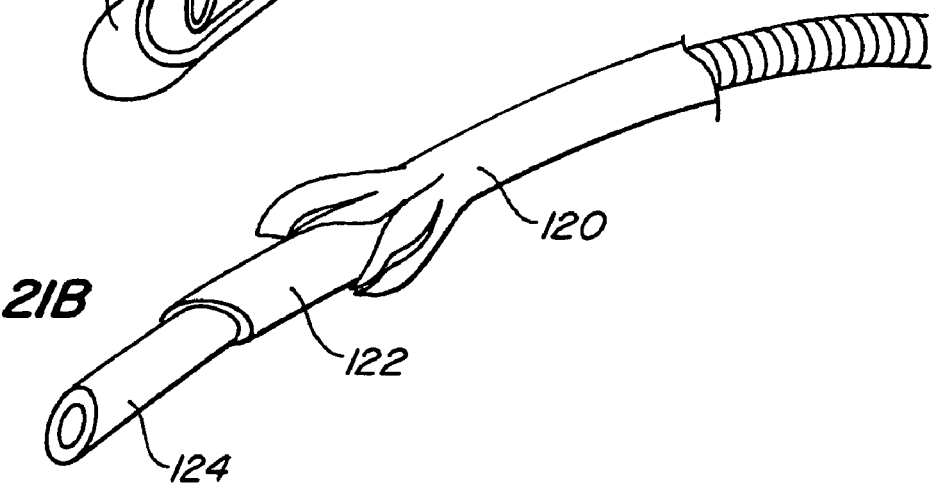

FIG. 21 shows a biopsy needle for use with bronchoscope systems such as those described above. As shown in FIG. 21A, a sleeve 120 covers needle 122 and center wire 124 during delivery and positioning of the needle. Sleeve 120 extends back proximally exterior of the patient and is advanced along with needle 122 and 124 through a needle guide disposed within a bronchoscope working channel or exterior to the bronchoscope. When the needle is to be used to gather a tissue sample, sleeve 120 is held stationary while needle 122 and center wire 124 are advanced distally (or sleeve 120 is drawn proximally while needle 122 and center wire 124 are held stationary) so that needle 122 and center wire 124 perforate sleeve 120, as shown in FIG. 21B. Needle 122 and center wire 124 are then used to gather a tissue sample.

Figure 22:
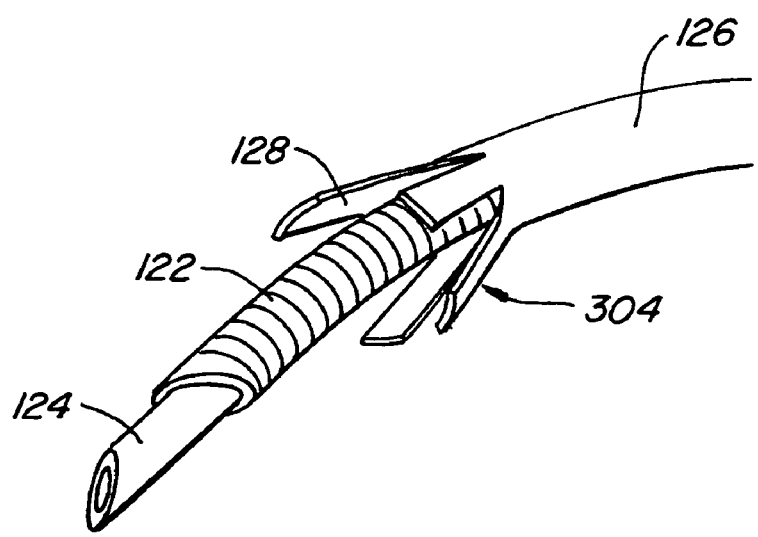
FIG. 22 shows a radially expandable sleeve covering a needle and a center wire or needle during delivery and positioning via a bronchoscope system.

In FIG. 22, a radially expandable sleeve 126 covers needle 122 and center wire or needle 124 during delivery and positioning via a bronchoscope system, as in the embodiment of FIG. 21A above. When at the biopsy site, the distal end of sleeve 126 is radially expanded as shown in FIG. 22 to permit needle 122 and center wire or needle 124 to pass through the distal end of sleeve 126. When the sleeve 126 is open, the radial wings 128 at the sleeve's distal end can perform several functions. Wings 128 provide a registration function when disposed against the bronchial wall so that the needle 122 and center wire or needle 124 can be advanced a controlled distance into and beyond the wall. Also, if the radial wings 128 are opened while the sleeve 126 is placed against tissue, movement of the wings can move aside and hold tissue to open a working area and fixate the device against the tissue. The radial wings can also be moved to a closed position after taking the tissue sample to help capture and contain the tissue sample.

FIGS. 23-25 show other embodiments of space-making devices that can be delivered via a bronchoscope system to provide working space for a biopsy or other procedure performed via a bronchoscope. In FIG. 23A, an expansion tool 130 is shown disposed in a closed configuration within an open-ended sleeve 132. After delivery via a bronchoscope system to a treatment site within a lung, expansion tool 132 may be operated to an open configuration to expand the open end 134 of sleeve 132. In this embodiment, pivoting arms 136 of tool 130 are moved apart against the inside of sleeve 132, as shown in FIG. 23B. After expansion of sleeve 132, expansion tool 130 may be removed to allow other tools to be delivered to the treatment site via sleeve 132. The expanded sleeve 132 may be used to stabilize the working area at the treatment site, to spread apart anatomical features at the treatment site and/or to help contain tissue samples.

FIGS. 24A and 24B show another embodiment of a space-making device. In FIG. 24A, an expansion tool 140 is being delivered to a treatment site via the working channel 42 of a bronchoscope 40. Expansion tool 140 is formed as a spiral. Once it emerges from the distal end of working channel 42, the spirals of expansion tool 140 unwind, as shown in FIG. 24B, to form a work space at the tool's distal end. Alternatively, expansion tool 140 may be delivered within a sleeve, and tool 140 may be used to expand the distal end of the sleeve, as in the embodiment of FIG. 23.

FIG. 25 shows yet another embodiment of a space-making device. As in the previous embodiment, expansion tool 150 is delivered to a treatment site via the working channel 42 of a bronchoscope 140. Once outside of the channel, an expansion portion 152 of tool 150 unwinds and expands radially to form a work space at the tool's distal end. As in the other embodiments, expansion tool 150 may be delivered within a sleeve, and tool 150 may be used to expand the distal end of the sleeve.

Figure 26:
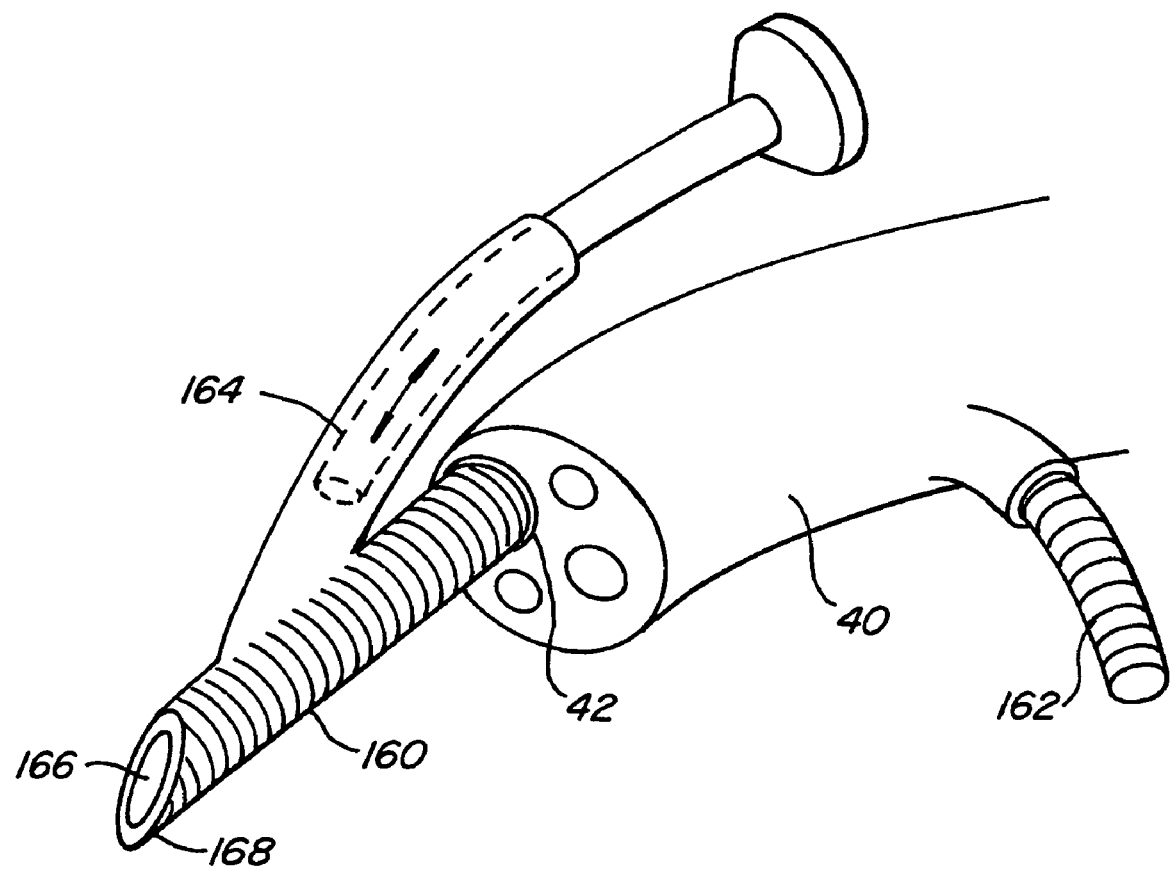
FIG. 26 shows a bifurcated cannula inserted into the distal end of the working channel of a bronchoscope prior to insertion of the bronchoscope into the patient.
Figure 27A:
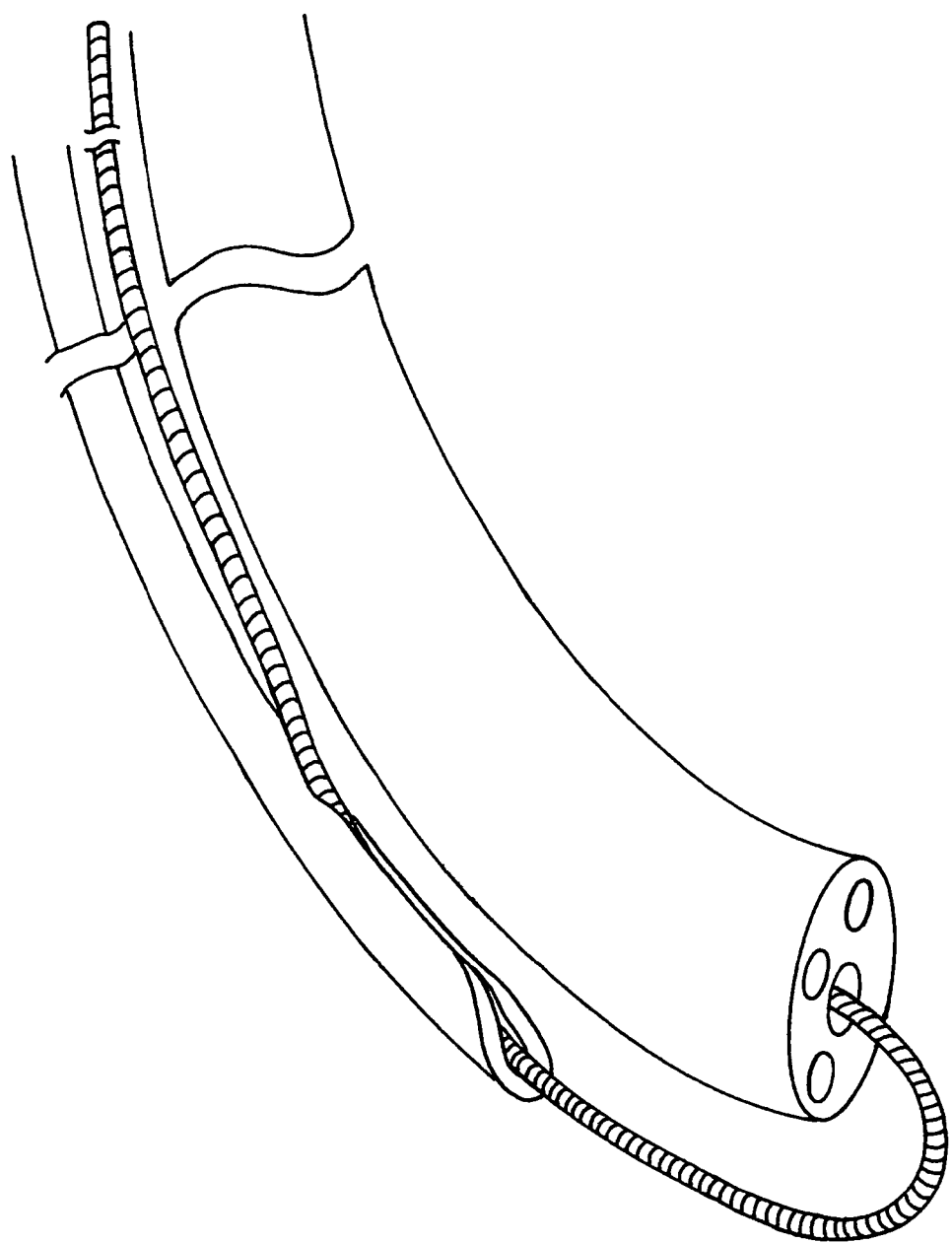
FIGS. 27A-D show a guide element connected to the instrument via a separable attachment device.
Figure 27B:
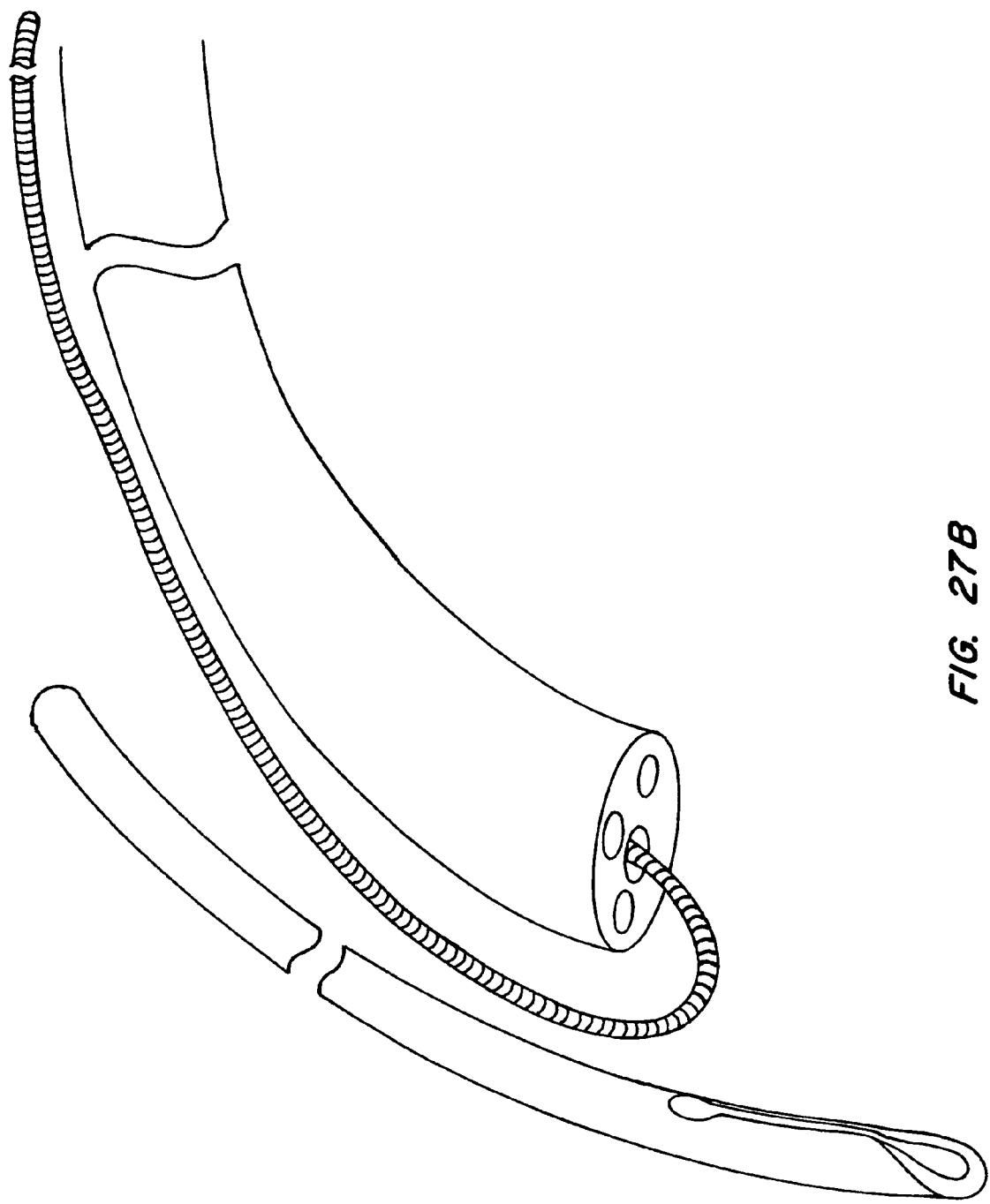
Figure 27C:
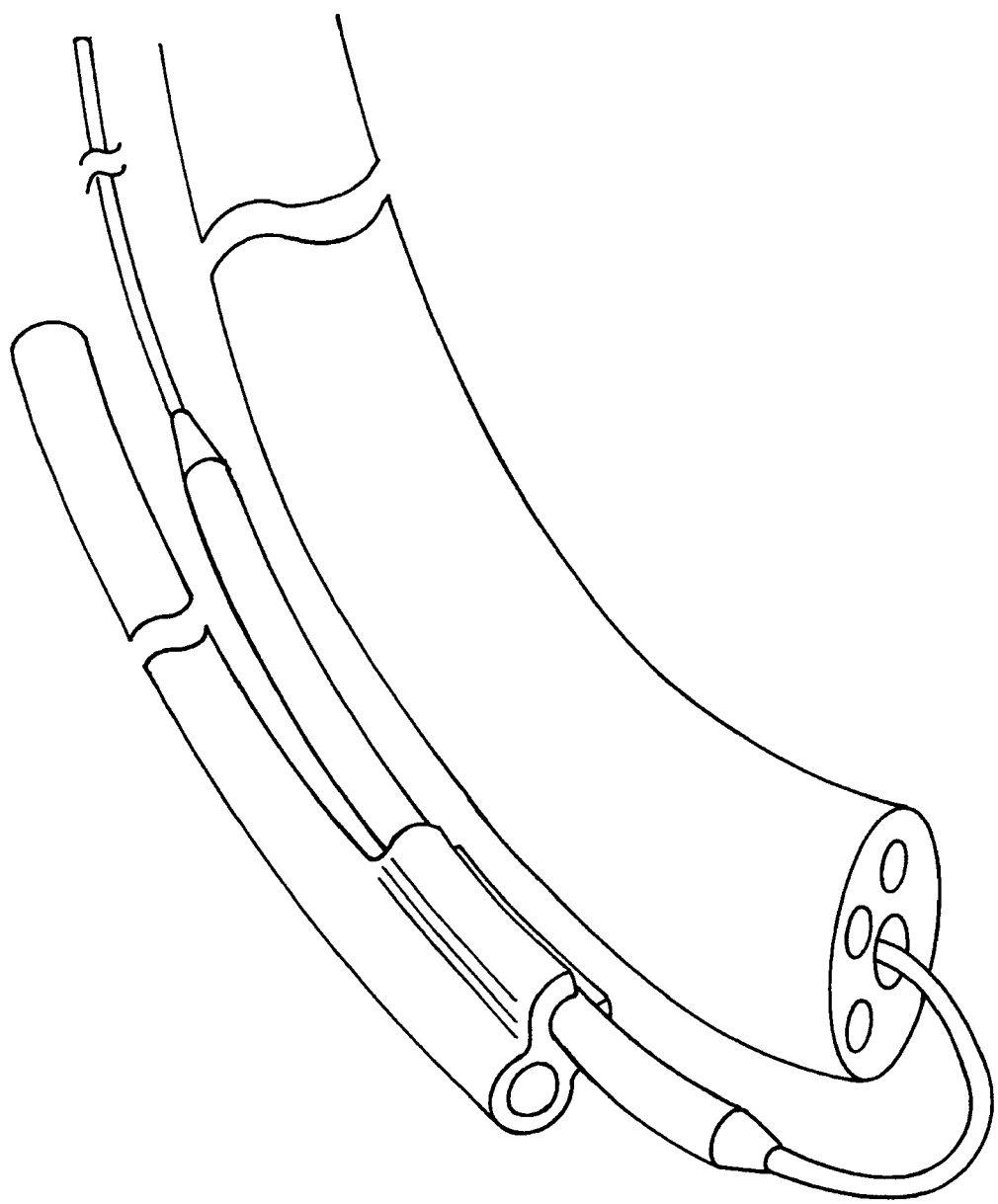
Figure 27D:
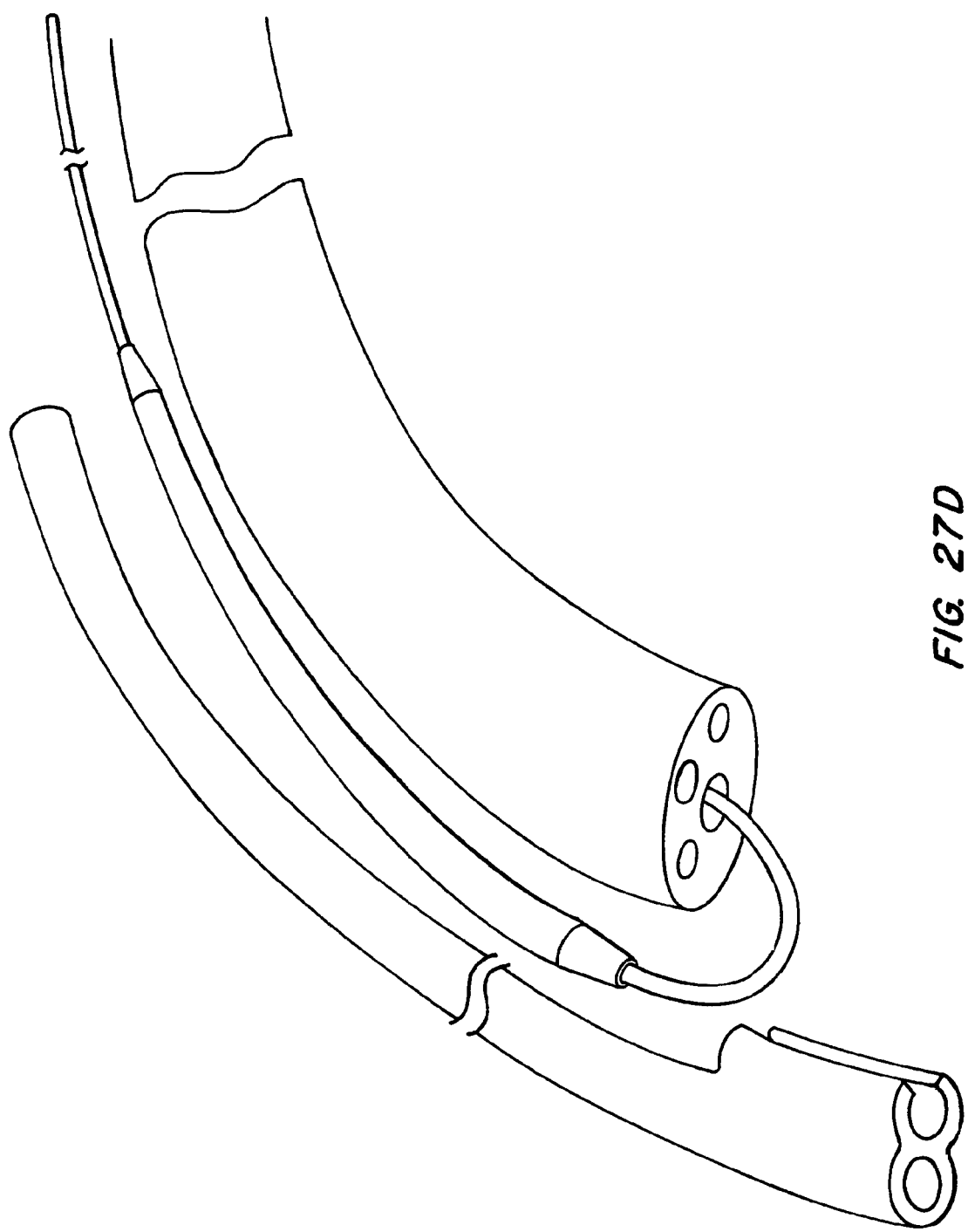

In FIG. 26, a bifurcated cannula 160 has been inserted into the distal end of the working channel 42 of a bronchoscope 40 prior to insertion of bronchoscope 40 into the patient. Cannula 160 provides two branches 162 and 164 for advancing tools to the same treatment site via distal port 166. As shown, branch 162 runs proximally along working channel 42, while branch 164 runs along the length of bronchoscope 40. The tip 168 surrounding port 166 may be sharp for penetrating tissue. For example, distal tip 168 may be pushed into the bronchial wall while the user observes the cannula's motion via a scope disposed in one of the lumens. The camera can then be pulled back so that a biopsy instrument can be advanced into that location. A marker can also be placed before, during or after taking the biopsy sample.

As an alternative to the use of a biopsy needle with the embodiments described above, a side collecting cutter tool may be used to collect tissue samples.

With respect to imaging, most pulmonology labs have real time fluoroscopy that can be quickly turned 90 degrees to confirm direction and depth. Alternatively, real time CAT scans can be used to image a cross-section of the patient's lungs and mediastinal region prior to biopsy or other procedures. If the image slice is narrowed to 3-5 mm and it cuts a plane transverse across the thorax, the user can visualize when the needle enters the plane and the 2D coordinates relative to the target. Unfortunately, real time CT equipment is not common. In another aspect of the invention, therefore, a very small radiopaque dye mark or metallic radiopaque marker may be delivered via a small transthoracic needle so the location can be confirmed and the mark can be used as an obvious landmark to direct a transbronchial needle aspiration system through a bronchoscope. Transthoracic delivery is generally much more accurate but the device profile would need to be small to avoid damaging the lung wall.

Yet another aspect of the invention is the use of endoscopes with access accessories to enter the mediastinal space to, e.g., obtain a tissue sample. The invention includes the use of glue or a plug (e.g., self-expanding stent, collagen plug, polymer plug, cyanoacrylates, glutaraldehyde formulations, polyethylene balloons to contain the glue, etc.) to close any holes in the lung wall or adjacent tissue in the event of pneumothorax.

In certain biopsy needle embodiments, the needle guide element or channel has a continuous channel through the center or side port with a constant lumen diameter and a close-fitting port dimension for precise biopsy device delivery. Radiopaque marker bands may be added at the port opening to facilitate imaging of the biopsy device with respect to the target tissue.

The invention claimed is:

1. A method of accessing a subject's lung or surrounding tissue of said subject's lung, the method comprising:
   (a) advancing a distal end of an imaging device into the subject's lung so that a proximal end of the imaging device is located outside said subject's lung;
   (b) positioning a guide element relative to the imaging device so that the guide element extends continuously from a first end of the guide element disposed adjacent the proximal end of the imaging device, distally through a lumen of the imaging device toward a distal end of the imaging device and then returning proximally from the distal end of the imaging device outside the imaging device to a second end of the guide element;
   (c) wherein the first and second ends of the guide element are disposed outside the lung after the imaging device is advanced so that the guide element between the second end and the distal end of the advanced imaging device is accessible to direct an instrument distally into the subject's lung; and
   (d) advancing the instrument over the guide element by receiving the second end of the guide element in a lumen of the instrument and advancing the instrument distally over the guide element from the second end to the distal end of the imaging device.

2. The method of claim 1, wherein more than one guide element returns proximally from the distal end of the imaging device outside the imaging device toward the proximal end of the imaging device so that an associated end of each guide element is accessible from outside the patient.

3. The method of claim 1, wherein said guide element has a distal end, wherein said distal end is adapted to be placed within a subject's body and is to be connected to said instrument.

4. The method of claim 1, wherein said guide element is a guide wire.

5. The method of claim 1, wherein said guide element comprises a needle guide.

6. The method of claim 1, further comprising tensioning of the guide element from outside the subject's lung so as to bend the guide element adjacent the distal end of the imaging device.

7. The method of claim 6, wherein the tensioning of the guide element comprising applying tension adjacent the second end of the guide element, and wherein the bending of the guide element is done so as to guide the imaging device with the bent guide element while advancing the imaging device into the subject's lung.

8. The method of claim 6, wherein the tensioning of the guide element comprises applying tension adjacent the second end of the guide element, and wherein the bending of the guide element is done so as to guide the instrument with the bent guide element while advancing the instrument into the subject's lung.

9. The method of claim 1, wherein the instrument has an outer diameter larger than a working channel diameter of the imaging device.

10. The method of claim 1, wherein said lumen of said imaging device comprises a working channel.

11. The method of claim 10, wherein at least a portion of said guide element is disposed inside said working channel.

12. The method of claim 10, further comprising an instrument connected to said guide element located outside said working channel.

13. The method of claim 12, wherein said instrument being connected to said guide element is located within or traversing said distal end of said working channel.

14. The method of claim 12, wherein said instrument is adapted to perform biopsy.

15. The method of claim 12, wherein said instrument is adapted to image bodily tissue.

16. The method of claim 12, wherein said instrument is adapted to deliver a pharmaceutical composition to the lung.

17. The method of claim 1, wherein said imaging device comprises a bronchoscope.

18. A method of accessing a subject's lung or surrounding tissue of said subject's lung, the method comprising:
   (a) advancing a distal end of an imaging device into the subject's lung so that a proximal end of the imaging device is located outside said subject's lung; and
   (b) positioning a guide element relative to the imaging device so that the guide element extends continuously from a first end of the guide element disposed adjacent the proximal end of the imaging device, distally through a lumen of the imaging device toward a distal end of the imaging device and then returning proximally from the distal end of the imaging device outside the imaging device to a second end of the guide element; and
   (c) wherein the first and second ends of the guide element are disposed outside the lung after the imaging device is advanced so that the guide element between the second end and the distal end of the advanced imaging device is accessible to direct an instrument distally into the subject's lung, and wherein said instrument comprises a needle guide.

19. The method of claim 18, wherein said needle guide comprises a side port.

20. A method of accessing a subject's lung or surrounding tissue of said subject's lung, the method comprising:
    (a) advancing a distal end of an imaging device into the subject's lung so that a proximal end of the imaging device is located outside said subject's lung; and
    (b) positioning a guide element relative to the imaging device so that the guide element extends continuously from a first end of the guide element disposed adjacent the proximal end of the imaging device, distally through a lumen of the imaging device toward a distal end of the imaging device and then returning proximally from the distal end of the imaging device outside the imaging device to a second end of the guide element; and
    (c) wherein the first and second ends of the guide element are disposed outside the lung after the imaging device is advanced so that the guide element between the second end and the distal end of the advanced imaging device is accessible to direct a balloon distally into the subject's lung.

21. The method of claim 20, wherein said balloon comprises a lumen with at least one side port.

22. A method of accessing a subject's lung or surrounding tissue of said subject's lung, the method comprising:
    (a) advancing a distal end of an imaging device into the subject's lung so that a proximal end of the imaging device is located outside said subject's lung; and
    (b) positioning a guide element relative to the imaging device so that the guide element extends continuously from a first end of the guide element disposed adjacent the proximal end of the imaging device, distally through a lumen of the imaging device toward a distal end of the imaging device and then returning proximally from the distal end of the imaging device outside the imaging device to a second end of the guide element; and
    (c) wherein the first and second ends of the guide element are disposed outside the lung after the imaging device is advanced so that the guide element between the second end and the distal end of the advanced imaging device is accessible to direct an instrument distally into the subject's lung, and wherein said instrument comprises a catheter connected to a balloon.

23. A method of accessing a subject's lung or surrounding tissue of said subject's lung, the method comprising:
    (a) advancing a distal end of an imaging device into the subject's lung so that a proximal end of the imaging device is located outside said subject's lung; and
    (b) positioning a guide element relative to the imaging device so that the guide element extends continuously from a first end of the guide element disposed adjacent the proximal end of the imaging device, distally through a lumen of the imaging device toward a distal end of the imaging device and then returning proximally from the distal end of the imaging device outside the imaging device to a second end of the guide element; and
    (c) wherein the first and second ends of the guide element are disposed outside the lung after the imaging device is advanced so that the guide element between the second end and the distal end of the advanced imaging device is accessible to direct an instrument distally into the subject's lung, and wherein said instrument comprises a plurality of needle guides covered by an extendable sleeve.

24. A method of accessing a subject's lung or surrounding tissue of said subject's lung, the method comprising:
    (a) advancing a distal end of an imaging device into the subject's lung so that a proximal end of the imaging device is located outside said subject's lung;
    (b) positioning a guide element relative to the imaging device so that the guide element extends continuously from a first end of the guide element disposed adjacent the proximal end of the imaging device, distally through a lumen of the imaging device toward a distal end of the imaging device and then returning proximally from the distal end of the imaging device outside the imaging device to a second end of the guide element;
    (c) wherein the first and second ends of the guide element are disposed outside the lung after the imaging device is advanced so that the guide element between the second end and the distal end of the advanced imaging device is accessible to direct an instrument distally into the subject's lung, and wherein the guide element has a lumen extending between the second and the distal end of the advanced imaging device; and
    (d) advancing the instrument from the second end of the guide element distally through the lumen of the guide element toward the distal end of the advanced imaging device.

* * * * *